United States Patent
Rajagopal et al.

(10) Patent No.: US 10,066,263 B2
(45) Date of Patent: Sep. 4, 2018

(54) NUCLEIC ACID REACTIONS AND RELATED METHODS AND COMPOSITIONS

(71) Applicant: California Institute of Technology, Pasadena, CA (US)

(72) Inventors: Aditya Rajagopal, Orange, CA (US); Emil P. Kartalov, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/623,974

(22) Filed: Jun. 15, 2017

(65) Prior Publication Data
US 2017/0362636 A1    Dec. 21, 2017

Related U.S. Application Data

(60) Provisional application No. 62/351,411, filed on Jun. 17, 2016.

(51) Int. Cl.
| | |
|---|---|
| *C12Q 1/68* | (2018.01) |
| *C12Q 1/686* | (2018.01) |
| *C07H 21/04* | (2006.01) |
| *G01N 21/64* | (2006.01) |

(52) U.S. Cl.
CPC ............. *C12Q 1/686* (2013.01); *C07H 21/04* (2013.01); *B01J 2219/00659* (2013.01); *G01N 2021/6417* (2013.01)

(58) Field of Classification Search
None
See application file for complete search history.

(56) References Cited

U.S. PATENT DOCUMENTS

| | | | |
|---|---|---|---|
| 5,079,351 A | 1/1992 | Sninsky et al. |
| 5,538,848 A | 7/1996 | Livak et al. |
| 5,618,711 A | 4/1997 | Gelfand et al. |
| 5,677,152 A | 10/1997 | Birch et al. |
| 5,723,591 A | 3/1998 | Livak et al. |
| 5,773,258 A | 6/1998 | Birch et al. |
| 5,789,224 A | 8/1998 | Gelfand et al. |
| 5,804,375 A | 9/1998 | Gelfand et al. |
| 5,876,930 A | 3/1999 | Livak et al. |
| 5,928,862 A | 7/1999 | Morrison |
| 5,948,360 A | 9/1999 | Rao et al. |
| 5,981,180 A | 11/1999 | Chandler et al. |
| 5,994,056 A | 11/1999 | Higuchi |
| 6,030,787 A | 2/2000 | Livak et al. |
| 6,127,155 A | 10/2000 | Gelfand et al. |
| 6,171,785 B1 | 1/2001 | Higuchi |
| 6,258,569 B1 | 7/2001 | Livak et al. |
| 6,534,266 B1 | 3/2003 | Singer |
| 6,548,259 B2 | 4/2003 | Ward et al. |
| 6,642,062 B2 | 11/2003 | Kauvar et al. |
| 7,101,663 B2 | 9/2006 | Godfrey et al. |
| 7,141,377 B2 | 11/2006 | Gelfand et al. |
| 7,348,141 B2 | 3/2008 | French et al. |
| 7,385,043 B1 | 6/2008 | Kramer |
| 7,410,764 B2 | 8/2008 | Gocke et al. |
| 7,413,708 B2 | 8/2008 | Mayrand |
| 7,473,767 B2 | 1/2009 | Dimitrov |
| 7,575,864 B2 | 8/2009 | Bedzyk et al. |
| 7,667,024 B2 | 2/2010 | Mao et al. |
| 7,767,423 B2 | 8/2010 | Kopreski |
| 7,771,949 B2 | 8/2010 | Kramer |
| 7,919,237 B2 | 4/2011 | Dimitrov et al. |
| 7,919,244 B2 | 4/2011 | Madejon et al. |
| 7,930,106 B2 | 4/2011 | Carrick |
| 7,941,279 B2 | 5/2011 | Hwang et al. |
| 8,039,215 B2 | 10/2011 | Higuchi et al. |
| 8,148,512 B2 | 4/2012 | Dimitrov |
| 8,426,132 B2 | 4/2013 | Li et al. |
| 8,455,184 B2 | 6/2013 | Atchley et al. |
| 8,492,094 B2 | 7/2013 | Dimitrov et al. |
| 8,519,115 B2 | 8/2013 | Webster et al. |
| 8,614,061 B2 | 12/2013 | Brabetz et al. |
| 8,771,955 B2 | 7/2014 | Reed et al. |
| 8,838,394 B2 | 9/2014 | Kartalov et al. |
| 8,877,464 B2 | 11/2014 | Babiel et al. |
| 8,962,250 B2 | 2/2015 | Stanley |
| 9,133,506 B2 | 9/2015 | Katzir et al. |
| 9,222,128 B2 | 12/2015 | Saxonov et al. |
| 9,260,761 B2 | 2/2016 | Tyagi et al. |
| 9,422,593 B2 | 8/2016 | Rothmann et al. |
| 9,447,457 B2 | 9/2016 | Chun et al. |
| 9,458,497 B2 | 10/2016 | Hassibi et al. |
| 2002/0022273 A1 | 2/2002 | Empedocles et al. |
| 2002/0146734 A1 | 10/2002 | Ortyn et al. |
| 2003/0148280 A1 | 8/2003 | Harris et al. |
| 2003/0148544 A1 | 8/2003 | Nie et al. |
| 2005/0064435 A1 | 3/2005 | Su et al. |
| 2005/0164264 A1 | 7/2005 | Shipwash |
| 2005/0214753 A1 | 9/2005 | Shultz et al. |
| 2005/0260640 A1 | 11/2005 | Andersen et al. |
| 2006/0216708 A1 | 9/2006 | Venema |
| 2007/0072211 A1 | 3/2007 | Newton et al. |
| 2007/0178485 A1 | 8/2007 | El-Deiry et al. |
| 2007/0231824 A1 | 10/2007 | Chee et al. |
| 2008/0050737 A1 | 2/2008 | Arieli et al. |
| 2008/0069733 A1 | 3/2008 | Maltezos et al. |
| 2008/0124705 A1 | 5/2008 | Kramer |
| 2009/0042735 A1 | 2/2009 | Blair et al. |
| 2009/0048785 A1 | 2/2009 | Katzir et al. |
| 2009/0062129 A1 | 3/2009 | McKernan et al. |

(Continued)

FOREIGN PATENT DOCUMENTS

| | | |
|---|---|---|
| CN | 101570782 A | 11/2009 |
| EP | 1448581 B1 | 11/2008 |

(Continued)

OTHER PUBLICATIONS

Gandelman et al, PLoS One 5 (11), e14155 (2010).*

(Continued)

Primary Examiner — James Martinell
(74) Attorney, Agent, or Firm — Wilson Sonsini Goodrich & Rosati

(57) ABSTRACT

The present invention relates to methods of nucleic acid analyte detection by PCR. In particular, methods and kits for the detection of a plurality of nucleic acid analytes and the generation of kinetic signatures are provided. Further provided are methods and kits of nested PCR and PCR using limiting primers.

3 Claims, 10 Drawing Sheets

(56) References Cited

U.S. PATENT DOCUMENTS

| | | |
|---|---|---|
| 2010/0015607 A1 | 1/2010 | Geiss et al. |
| 2010/0047924 A1 | 2/2010 | Webster et al. |
| 2010/0112710 A1 | 5/2010 | Geiss et al. |
| 2010/0151443 A1 | 6/2010 | Xiang et al. |
| 2010/0159447 A1 | 6/2010 | Li et al. |
| 2010/0210472 A1 | 8/2010 | Empedocles et al. |
| 2010/0233686 A1 | 9/2010 | Higuchi et al. |
| 2010/0248257 A1 | 9/2010 | Jacobsen et al. |
| 2010/0261026 A1 | 10/2010 | Ferree et al. |
| 2010/0267064 A1 | 10/2010 | Kartalov et al. |
| 2010/0273173 A1 | 10/2010 | Hirai et al. |
| 2011/0104684 A1 | 5/2011 | Hooper |
| 2011/0151459 A1 | 6/2011 | Rothmann et al. |
| 2011/0151550 A1 | 6/2011 | Sagner et al. |
| 2011/0207623 A1 | 8/2011 | Dimitrov et al. |
| 2011/0237459 A1 | 9/2011 | Nova et al. |
| 2012/0003646 A1 | 1/2012 | Joo et al. |
| 2012/0040349 A1 | 2/2012 | Von Lode et al. |
| 2012/0045756 A1 | 2/2012 | Rothmann et al. |
| 2012/0077195 A1 | 3/2012 | Li et al. |
| 2012/0122704 A1 | 5/2012 | Atchley et al. |
| 2012/0141995 A1 | 6/2012 | Li et al. |
| 2012/0171677 A1 | 7/2012 | Ludowise |
| 2012/0184017 A1 | 7/2012 | Chatterjee |
| 2012/0190030 A1 | 7/2012 | Chun et al. |
| 2012/0196283 A1 | 8/2012 | Babiel et al. |
| 2012/0252017 A1 | 10/2012 | Reed et al. |
| 2012/0258457 A1 | 10/2012 | Jarosch et al. |
| 2013/0017971 A1 | 1/2013 | Geiss et al. |
| 2013/0040841 A1 | 2/2013 | Saxonov et al. |
| 2013/0116780 A1 | 5/2013 | Miller et al. |
| 2013/0261019 A1 | 10/2013 | Lin et al. |
| 2014/0038195 A1 | 2/2014 | Malik et al. |
| 2014/0171341 A1 | 6/2014 | Jouvenot et al. |
| 2014/0213471 A1 | 7/2014 | Rajagopal et al. |
| 2015/0057178 A1 | 2/2015 | Kartalov et al. |
| 2015/0140554 A1 | 5/2015 | Snyder et al. |

FOREIGN PATENT DOCUMENTS

| | | |
|---|---|---|
| EP | 1963531 B1 | 9/2011 |
| EP | 1629108 B1 | 12/2014 |
| WO | WO-9919515 A1 | 4/1999 |
| WO | WO-9952708 A1 | 10/1999 |
| WO | WO-02056014 A2 | 7/2002 |
| WO | WO-03002979 A2 | 1/2003 |
| WO | WO-02056014 A3 | 10/2003 |
| WO | WO-2004087950 A2 | 10/2004 |
| WO | WO-2006079049 A2 | 7/2006 |
| WO | WO-2007076128 A2 | 7/2007 |
| WO | WO-2007076129 A2 | 7/2007 |
| WO | WO-2007076132 A2 | 7/2007 |
| WO | WO-2007076132 A3 | 9/2007 |
| WO | WO-2007076128 A3 | 11/2007 |
| WO | WO-2007139766 A2 | 12/2007 |
| WO | WO-2007076129 A3 | 3/2008 |
| WO | WO-2008124847 A2 | 10/2008 |
| WO | WO-2007139766 A3 | 12/2008 |
| WO | WO-2008124847 A3 | 2/2009 |
| WO | WO-2010019826 A1 | 2/2010 |
| WO | WO-2010128206 A1 | 11/2010 |
| WO | WO-2011047087 A2 | 4/2011 |
| WO | WO-2011047087 A3 | 8/2011 |
| WO | WO-2011100541 A2 | 8/2011 |
| WO | WO-2011116088 A2 | 9/2011 |
| WO | WO-2011100541 A3 | 1/2012 |
| WO | WO-2011116088 A3 | 2/2012 |
| WO | WO-2012058638 A2 | 5/2012 |
| WO | WO-2012106428 A2 | 8/2012 |
| WO | WO-2012135340 A2 | 10/2012 |
| WO | WO-2012058638 A3 | 12/2012 |
| WO | WO-2012135340 A3 | 12/2012 |
| WO | WO-2013096851 A1 | 6/2013 |
| WO | WO-2013116780 A1 | 8/2013 |
| WO | WO-2017173035 A1 | 10/2017 |

OTHER PUBLICATIONS

Holland, et al., Detection of specific polymerase chain reaction product by utilizing the 5' to 3' exonuclease activity of Thermus aquaticus DNA polymerase. PNAS (USA) 88:7276-7280, 1991.

Beige, et al. Clinical evaluation of a *Mycobacterium tuberculosis* PCR assay. J Clin Microbiol. Jan. 1995;33(1):90-5.

Chamberlain, et al. Deletion screening of the Duchenne muscular dystrophy locus via multiplex DNA amplification. Nucleic Acids Res. Dec. 9, 1988;16(23):11141-56.

Chapin et al., Rapid microRNA profiling on encoded gel microparticles. Angewandte Chemie International Edition, 50(10):2289-2293, 2011.

Chen, et al. A Homogeneous, ligase-mediated DNA diagnostic test. Genome Research, 1998, vol. 8, pp. 549-556.

Chong, et al. Single-tube multiplex-PCR screen for common deletional determinants of alpha-thalassemia. Blood. Jan. 1, 2000;95(1):360-2.

Chromatogram, 2011, 2 pages. Dorland's illustrated medical dictionary. Retrieved online on Jan. 22, 2014 from «http://www.credoreference.com».

Chun, et al. Dual priming oligonucleotide system for the multiplex detection of respiratory viruses and SNP genotyping of CYP2C19 gene. Nucleic Acids Res. 2007;35(6):e40. Epub Feb. 7, 2007.

Craig, et al. Ordering of cosmid clones covering Herpes simplex virus type I (HSV-I) genome: a test case for fingerprinting by hybridisation. Nucleic Acids Research, 1990, vol. 18, pp. 2653-2660.

Dos Santos, et al. A simple one-step real-time RT-PCR for diagnosis of dengue virus infection. J Med Virol. Aug. 2008;80(8):1426-33. doi: 10.1002/jmv.21203.

El-Hajj, et al. Detection of rifampin resistance in *Mycobacterium tuberculosis* in a single tube with molecular beacons. J Clin Microbiol. Nov. 2001;39(11):4131-7.

EMBL-Bank: AJ303204. http://www.ebi.ac.uk/Tools/dbfetch/emblfetch?db=embl&id=AJ303204&format=default&style=default&Retrieve=Retrieve. Accessed Feb. 2012.

EMBL-Bank: GQ395623. http://www.ebi.ac.uk/Tools/dbfetch/emblfetch?db=embl&id=GQ395623&format=default&style=default&Retrieve=Retrieve. Accessed Feb. 2012.

European Patent Application No. 13744261.2 Extended European Search Report dated May 3, 2016.

Fodor, et al. Multiplexed biochemical assays with biological chips. Nature. Aug. 5, 1993;364(6437):555-6.

Fortina, et al. Digital mRNA profiling. Nat Biotechnol. Mar. 2008;26(3):293-4. doi: 10.1038/nbt0308-293.

GenBank: M93130.1. Dengue type 3 virus complete genome RNA, complete cds. http://www.ncbi.nlm.nih.gov/nuccore/M93130. Accessed Feb. 2012.

Han, et al. Quantum-dot-tagged microbeads for multiplexed optical coding of biomolecules. Nat Biotechnol. Jul. 2001;19(7):631-5.

Hartman, et al. Development of a novel internal positive control for Taqman based assays. Mol Cell Probes. Feb. 2005;19(1):51-9. Epub Dec. 10, 2004.

Heidari, et al. Detection of Plasmodium falciparum Directly from Blood Samples Using the Polymerase Chain Reaction. Journal of Sciences, Islamic Republic of Iran. 2005 16(1):21-24.

Henegariu, et al. Multiplex PCR: critical parameters and step-by-step protocol. Biotechniques. Sep. 1997;23(3):504-11.

HIV databases. http://www.hiv.lanl.gov/content/index. Accessed Feb. 2012.

Horejsh, et al. A molecular beacon, bead-based assay for the detection of nucleic acids by flow cytometry. Nucleic Acids Res. Jan. 19, 2005;33(2):e13.

Huang, et al. Identification of 8 foodborne pathogens by multicolor combinational probe coding technology in a single real-time PCR. Clin Chem. Oct. 2007;53(10):1 741-8. Epub Aug. 10, 2007.

Huang, et al. Multicolor combinatorial probe coding for real-time PCR. PLoS One. Jan. 14, 2011;6(1):e16033. doi: 10.1371/journal.pone.0016033.

International search report and written opinion dated Apr. 12, 2013 for PCT/US2013/024509.

(56) References Cited

OTHER PUBLICATIONS

International search report and written report dated Jun. 22, 2017 for PCT Application No. PCT/US2017/24933.
Jothikumar, et al. Design of FRET-TaqMan probes for multiplex real-time PCR using an internal positive control. Biotechniques. Jun. 2009;46(7):519-24. doi: 10.2144/000113127.
Klostranec et al., Convergence of quantum dot barcodes with microfluidics and signal processing for multiplexed high-throughout infectious disease diagnostics. Nano Letters, 7(9):2812-2818, 2007.
Kuhn, et al. Hybridization of DNA and PNA molecular beacons to single-stranded and double-stranded DNA targets. J Am Chem Soc. Feb. 13, 2002;124(6):1097-103.
Lao, et al. Multiplexing RT-PCR for the detection of multiple miRNA species in small samples. Biochem Biophys Res Commun. Apr. 28, 2006;343(1):85-9. Epub Feb. 28, 2006.
Lee, et al. Novel multiplex PCR using dual-priming oligonucleotides for detection and discrimination of the *Mycobacterium tuberculosis* complex and M. bovis BCG. J Clin Microbiol. Dec. 2010;48(12):4612-4. doi: 10.1128/JCM.00872-10. Epub Oct. 13, 2010.
Lee, et al. Seven-color, homogeneous detection of six PCR products. Biotechniques. Aug. 1999;27(2):342-9.
Li et al., Multiplexed detection of pathogen DNA with DNA-based fluorescence nanobarcodes. Nature Biotechnology, 23(7):885-889, 2005.
Liew, et al. Validating a custom multiplex ELISA against individual commercial immunoassays using clinical samples. Biotechniques. Mar. 2007;42(3):327-8, 330-3.
Lin et al., Self-assembled combinatorial encoding nanoarrays for multiplexed biosensing. Nano Letters, 7(2):507-512, 2007.
Livak, et al. Oligonucleotides with fluorescent dyes at opposite ends provide a quenched probe system useful for detecting PCR product and nucleic acid hybridization. PCR Methods Appl. Jun. 1995;4(6):357-62.
Morrison, et al. Two-color ratio-coding of chromosome targets in fluorescence in situ hybridization: quantitative analysis and reproducibility. Cytometry. Apr. 1, 1997;27(4):314-26.
Noordhoek, et al. Sensitivity and specificity of PCR for detection of *Mycobacterium tuberculosis*: a blind comparison study among seven laboratories. J Clin Microbiol. Feb. 1994;32(2):277-84.
Notice of allowance dated Jun. 2, 2014 for U.S. Appl. No. 13/756,760.
Office action dated Jan. 24, 2014 for U.S. Appl. No. 13/756,760.
Office action dated Jun. 6, 2017 for U.S. Appl. No. 14/451,876.
Office action dated Nov. 23, 2016 for U.S. Appl. No. 14/451,876.
Oliveira, et al. Multiplex PCR strategy for rapid identification of structural types and variants of the mec element in methicillin-resistant *Staphylococcus aureus*. Antimicrob Agents Chemother. Jul. 2002;46(7):2155-61.
Ou, et al. DNA amplification for direct detection of HIV-1 in DNA of peripheral blood mononuclear cells. Science. Jan. 15, 1988;239(4837):295-7.
Paton, et al. Detection and characterization of Shiga toxigenic *Escherichia coli* by using multiplex PCR assays for stx1, stx2, eaeA, enterohemorrhagic *E. coli* hlyA, rfbO111, and rfbO157. J Clin Microbiol. Feb. 1998;36(2):598-602.
Patterson, et al. Detection of HIV-1 DNA and messenger RNA in individual cells by PCR-driven in situ hybridization and flow cytometry. Science. May 14, 1993;260(5110):976-9.
Petersen, et al. Short PNA molecular beacons for real-time PCR allelic discrimination of single nucleotide polymorphisms. Mol Cell Probes. Apr. 2004;18(2):117-22.
Plasmodium falciparum (Plasmodium falciparum) Genome Browser Gateway. http://microbes.ucsc.edu/cgi-bin/hgGateway?hgsid=612764&clade=eukaryota-protista&org=0&db=0. Accessed Feb. 2012.
Ptak, et al. Inhibition of human immunodeficiency virus type 1 replication in human cells by Debio-025, a novel cyclophilin binding agent. Antimicrob Agents Chemother. Apr. 2008;52(4):1302-17. doi: 10.1128/AAC.01324-07. Epub Jan. 22, 2008.
Rosenstraus, et al. An internal control for routine diagnostic PCR: design, properties, and effect on clinical performance. J Clin Microbiol. Jan. 1998;36(1):191-7.
Roth, et al. Feasibility and efficacy of routine PCR screening of blood donations for hepatitis C virus, hepatitis B virus, and HIV-1 in a blood-bank setting. Lancet. Jan. 30, 1999;353(9150):359-63.
Sambrook, et al. Molecular Cloning: A Laboratory Manual. 2nd Edition, 1989, pp. xi-xxxviii.
Sanger, et al. DNA sequencing with chain-terminating inhibitors. Proc Natl Acad Sci U S A. Dec. 1977;74(12):5463-7.
Speicher, et al. Karyotyping human chromosomes by combinatorial multi-fluor FISH. Nat Genet. Apr. 1996;12(4):368-75.
Tirasophon, et al. A novel detection of a single Plasmodium falciparum in infected blood. Biochem Biophys Res Commun. Feb. 28, 1991;175(1):179-84.
Tyagi, et al. Multicolor molecular beacons for allele discrimination. Nat Biotechnol. Jan. 1998;16(1):49-53.
Tyagi, et al. Wavelength-shifting molecular beacons. Nat Biotechnol. Nov. 2000;18(11):1191-6.
Urdea, et al. Requirements for high impact diagnostics in the developing world. Nature. Nov. 23, 2006;444 Suppl 1:73-9.
Vet, et al. Multiplex detection of four pathogenic retroviruses using molecular beacons. Proc Natl Acad Sci U S A. May 25, 1999;96(11):6394-9.
Wang, et al. Locked nucleic acid molecular beacons. J Am Chem Soc. Nov. 16, 2005;127(45):15664-5.
Waters, et al. Microchip device for cell lysis, multiplex PCR amplification, and electrophoretic sizing. Anal Chem. Jan. 1, 1998;70(1):158-62.
Weidmann, et al. Rapid detection of herpes simplex virus and varicella-zoster virus infections by real-time PCR. J Clin Microbiol. Apr. 2003;41(4):1565-8.
Wiese, et al. Simultaneous multianalyte ELISA performed on a microarray platform. Clin Chem. Aug. 2001;47(8):1451-7.
Xu et al., Multiplexed SNP genotyping using the Qbead system: a quantum dot-encoded microspere-based assay. Nucleic Acids Research, 31(8):e43, 2003.
Zhang, et al. Novel Multiplex PCR Assay for Characterization and Concomitant Subtyping of *Staphylococcal cassette* Chromosome mec Types I to V in Methicillin-Resistant *Staphylococcus aureus*. J Clin Microbiol. Oct. 2005;43(10):5026-33.
International Search Report and Written Opinion dated Nov. 16, 2017 for International PCT Patent Application No. PCT/US2017/37682.
Co-pending U.S. Appl. No. 15/914,356, filed Mar. 7, 2018.
U.S. Appl. No. 15/677,772 Office Action dated Feb. 8, 2018.

* cited by examiner

NUCLEIC ACID REACTIONS AND RELATED METHODS AND COMPOSITIONS

CROSS-REFERENCE

This application claims the benefit of U.S. Provisional Application No. 62/351,411, filed Jun. 17, 2016, which is incorporated by reference herein in its entirety.

BACKGROUND

The polymerase chain reaction is a technique that is used for increasing the quantity of a nucleic acid target. By thermal cycling a reaction cocktail of short primer sequences, free nucleotides and DNA polymerase, a template strand can be copied. For the polymerase chain reaction (PCR), temperature plateaus are often required: a high temperature for denaturation of the amplicon of interest, a low temperature for the binding of primers to the template, and an intermediate temperature for the synthesis of a complement strand.

Specificity of the binding between the primers and the template allows for selective amplification of intended targets. For instance, a typical quantitative polymerase chain reaction is run to "saturation," wherein the amplification reaction is run to the point at which at least one of the reactants such as primers, polymerase, probe, or free nucleotides is exhausted. When fluorescent reporters such as TaqMan probes, FRET probes, or intercalating dyes are used to interpret the extent of the DNA amplification, a fluorescence curve could be generated. The sigmoidal signature of a "saturation" fluorescence curve often occurs when the reporter probe concentrations are depleted at an ever-increasing rate.

However, this reaction (and by extension, its signature fluorescence) is limited by all reactant concentrations, including the PCR primers. As an example, when a single set of primers is used in equal concentrations, and when one primer is more efficiently extended than the other, the reaction becomes rate limited. This results in a linear, as compared to an exponential, amplification of DNA.

SUMMARY OF THE INVENTION

Described herein, in some embodiments, are methods of detecting the presence or absence of a target nucleic acid analyte in a sample, the methods comprising a) performing an amplification reaction on the sample; b) measuring a signal generated during the amplification reaction and generating a kinetic signature from the measured signal; and c) comparing the generated kinetic signature to a reference signature and determining whether the generated kinetic signature corresponds with the reference signature, thereby detecting the presence or absence of the target nucleic acid analyte in the sample. In some embodiments, kinetic signature comprises a signal selected from an electromagnetic signal, a wavelength, and a fluorescence emission signal. In some embodiments, the kinetic signature is plotted as a curve. In some embodiments, the curve comprises at least one of an exponential region, a linear region, and a plateau region. In some embodiments, the kinetic signature comprises recorded values. In some embodiments, the values are recorded in a table. In some embodiments, the amplification reaction is a polymerase chain reaction (PCR). In some embodiments, the reference signature corresponds with a kinetic signature generated by amplification of the target nucleic acid analyte under one or more members of a set of constrained amplification parameters. In some embodiments, the set of constrained amplification parameters comprises any combination of: (i) a range of forward and/or reverse primer concentrations; (ii) a range of polymerase concentrations; (iii) polymerase type; (iv) a range of nucleotide concentrations; (v) chromophore concentration; and (vi) chromophore type; (vii) a number of thermocycles; (viii) rate of thermocycling; (ix) one or more thermocycle stage temperatures; and (x) one or more thermocycle stage time lengths; (xi) a range of target-specific molecular probes; (xii) primers associated with one or more target-specific probes; and (xiii) a concentration of one or more enzyme cofactors. In some embodiments, the amplification reaction is carried out within one or more of the constrained amplification parameters.

Described herein, in some embodiments, are methods of detecting the presence or absence of a target nucleic acid analyte in a sample, the method comprising a) performing an amplification reaction on the sample under a set of constrained amplification parameters, the set comprising any combination of one or more of (i) a range of forward and/or reverse primer concentrations; (ii) a range of polymerase concentrations; (iii) polymerase type; (iv) a range of nucleotide concentrations; (v) chromophore concentration; (vi) chromophore type; (vii) number of thermocycles; (viii) rate of thermocycling; (ix) one or more thermocycle stage temperatures; and (x) one or more thermocycler stage time lengths; (xi) a range of target-specific molecular probes; and (xii) primers associated with one or more target-specific probes; and (xiii) a concentration of one or more enzyme cofactors; b) measuring a signal generated during the amplification reaction and generating a kinetic signature from the measured signal; c) comparing the generated kinetic signature to a reference signature, the reference signature corresponding with amplification of the target nucleic acid analyte under the set of constrained amplification parameters; and d) determining whether the generated kinetic signature corresponds with the reference signature, thereby detecting the presence or absence of the target nucleic acid analyte in the sample. In some embodiments, the amplification reaction is carried out within one or more of the constrained amplification parameters. In some embodiments, the one or more enzyme cofactors is selected from the group consisting of magnesium, potassium, and sodium. In some embodiments, the nucleic acid analyte is from a source selected from the group consisting of an animal, a plant, a bacterium, a parasite, and a virus. In some embodiments, the animal is a human. In some embodiments, the nucleic acid analyte is selected from the group consisting of human immunodeficiency virus, herpes simplex virus, human papilloma virus, *Plasmodium, Mycobacterium*, dengue virus, hepatitis virus, and influenza virus. In some embodiments, the nucleic acid analyte is selected from the group consisting of human immunodeficiency virus polyprotease, human immunodeficiency virus p17, human papilloma virus E6, and human papilloma virus E7. In some embodiments, the at least one of an exponential region, a linear region, and a plateau region occurs over at least 4 cycles. In some embodiments, the at least one of an exponential region, a linear region, and a plateau region occurs over at least 8 seconds.

Described herein, in some embodiments, are methods of detecting the presence or absence of each of a plurality of target nucleic acid analytes in a sample, the method comprising a) adding a primer set, the primer set comprising at least two primer pairs, to the sample, at least one of the primer pairs comprising a limiting primer, and each primer pair defining a region of one of the target nucleic acid analytes to be amplified; performing an amplification reaction on the sample; b) measuring a signal generated during the amplification reaction; and c) making a determination as to whether each of the plurality of target nucleic acid analytes is present based on the measured signal. In some embodiments, step c) further comprises a step of generating a kinetic signature from the measured signal, and step d) further comprises a step of comparing the kinetic signature to a reference signature, the reference signature corresponding with a kinetic signature generated by an amplification of one or more of the plurality of target nucleic acid analytes with the primer set, thereby making the determination. In some embodiments, the primer set consists of three primers. In some embodiments, the three primers consist of one forward primer and two reverse primers or two forward primers and one reverse primer. In some embodiments, the primer set comprises two or more nested primers. In some embodiments, the signal is generated by exciting a molecule that binds an amplification product. In some embodiments, the molecule is a hybridization probe. In some embodiments, (A) the primer set comprises first and second primer pairs, the first primer pair having a first annealing temperature and the second primer pair having a second annealing temperature which is lower than the first annealing temperature, and the first primer pair defining a region of one of the target nucleic acid analytes, the second primer pair defining a region of another of the nucleic acid analytes; and (B) the amplification reaction comprises thermocycling of a set of temperature cycles comprising at least one temperature cycle having a minimum temperature which is both (i) not greater than the first annealing temperature, and (ii) greater than the second annealing temperature, the reaction further comprising at least one other temperature cycle having a minimum temperature which is not greater than the second annealing temperature. In some embodiments, the amplification reaction comprises at least one temperature cycle which has a minimum temperature not greater than the first annealing temperature and greater than the second annealing temperature, followed by at least one temperature cycle which has a minimum temperature not greater than the second annealing temperature. In some embodiments, the amplification reaction comprises at least one temperature cycle which has a minimum temperature not greater than the second annealing temperature, followed by at least one temperature cycle which has a minimum temperature which is both (x) not greater than the first annealing temperature and (y) greater than the second annealing temperature. In some embodiments, step c) further comprises a step of generating a kinetic signature from the measured signal, and step d) further comprises a step of comparing the kinetic signature to a reference signature, the reference signature corresponding to a signal generated when one or more of the plurality of target nucleic acid analytes is amplified with the primer set by a thermocycling reaction comprising the set of temperature cycles, thereby making the determination. In some embodiments, the signal comprises a kinetic signature. In some embodiments, the kinetic signature comprises a signal selected from an electromagnetic signal, a wavelength, and a fluorescence emission signal. In some embodiments, the kinetic signature is plotted as a curve. In some embodiments, the curve comprises at least one of an exponential region, a linear region, or a plateau region. In some embodiments, the kinetic signature comprises recorded values. In some embodiments, the values are recorded in a table. In some embodiments, the limiting primer is present at a concentration sufficiently lower than the concentration of a non-limiting primer to generate a characteristic signal.

In some embodiments, the limiting primer is present at a concentration sufficiently lower that the concentration of a non-limiting primer to generate a characteristic kinetic signature. In some embodiments, the kinetic signature comprises a signal selected from an electromagnetic signal, a wavelength, and a fluorescence emission signal. In some embodiments, the kinetic signature is plotted as a curve. In some embodiments, the curve comprises at least one of an exponential region, a linear region, or a plateau region. In some embodiments, the kinetic signature comprises recorded values. In some embodiments, the values are recorded in a table. In some embodiments, the first and/or second annealing temperatures are determined by the limiting primer. In some embodiments, one or more primer of the primer pairs is linked to an antibody.

Described herein, in some embodiments, are methods of detecting the presence or absence of each of a plurality of target nucleic acid analytes in a sample, the methods comprising a) adding a primer set, the primer set comprising at least two primers, to the sample, at least one of the primer pairs comprising a limiting primer, and each primer pair defining a region of one of the target nucleic acid analytes to be amplified; b) performing a thermocycling amplification reaction on the sample, the reaction comprising a set of temperature cycles comprising at least one temperature cycle having a minimum temperature which is both (i) not greater than the first annealing temperature, and (ii) greater than the second annealing temperature, the reaction further comprising at least one other temperature cycle having a minimum temperature which is not greater than the second annealing temperature; c) measuring a signal generated during the amplification reaction; and d) making a determination as to whether each of the plurality of nucleic acid analytes is present based on the measured signal. In some embodiments, one or more primer of the primer pairs is linked to an antibody.

Described herein, in some embodiments, are methods of detecting the presence or absence of two or more of a plurality of target nucleic acid analytes in a sample, the methods comprising a) adding a primer set comprising first and second primer pairs to the sample, the first primer pair having a first annealing temperature and the second primer pair having a second annealing temperature which is lower than the first annealing temperature, and the first primer pair defining a region of one of the target nucleic acid analytes, the second primer pair defining a region of another of the nucleic acid analytes; b) performing a thermocycling amplification reaction on the sample, the reaction comprising a set of temperature cycles comprising at least one temperature cycle having a minimum temperature which is both (i) not greater than the first annealing temperature, and (ii) greater than the second annealing temperature, the reaction further comprising at least one other temperature cycle having a minimum temperature which is not greater than the second annealing temperature; c) measuring a signal generated during the amplification reaction; and d) making a determination as to the presence or absence of the two or more of the nucleic acid analytes based on the generated signal. In some embodiments, step c) further comprises a step of generating a kinetic signature from the measured signal, and step d) further comprises a step of comparing the kinetic signature to a reference signature, the reference signature corresponding with a signal generated when one or more of the plurality of target nucleic acid analytes is amplified with the primer set by a thermocycling reaction comprising the set of temperature cycles, thereby making the determination. In some embodiments, the first and second primer pairs comprise three primers. In some embodiments, the three primers comprise one forward primer and two reverse primers. In some embodiments, the three primers comprise two forward primers and one reverse primer. In some embodiments, the primer set comprises at least one pair of nested primers. In some embodiments, the amplification reaction comprises at least one temperature cycle which has a minimum temperature not greater than the first annealing temperature and greater than the second annealing temperature, followed by at least one temperature cycle which has a minimum temperature not greater than the second annealing temperature. In some embodiments, the amplification reaction comprises at least one temperature cycle which has a minimum temperature not greater than the second annealing temperature, followed by at least one temperature cycle which has a minimum temperature which is both (x) not greater than the first annealing temperature and (y) greater than the second annealing temperature. In some embodiments, at least one of the primer pairs comprises a limiting primer. In some embodiments, the limiting primer is present at a concentration of less than 1 □M. In some embodiments, a non-limiting primer is present at an initial concentration of at least two times greater than the limiting primer. In some embodiments, the limiting primer has a concentration-adjusted melting temperature that is equal to or greater than a non-limiting primer. In some embodiments, the signal is generated by a molecule that binds an amplification product. In some embodiments, the molecule is a hybridization probe. In some embodiments, the minimum temperature corresponds to the annealing temperature of first and second primer pairs. In some embodiments, the method comprises detecting the presence of n target nucleic acid analytes using n primer pairs, each primer pair having a different annealing temperature from that of the other primer pairs, and the set of temperature cycles comprising a set of minimum temperatures that are interspersed between the different annealing temperatures. In some embodiments, n is 3. In some embodiments, n is 4. In some embodiments, n is 5. In some embodiments, n is 6. In some embodiments, n is 7. In some embodiments, one or more primer of a primer pair is linked to an antibody.

Described herein, in some embodiments, are methods of detecting the presence or absence of each of a plurality of target nucleic acid analytes in a sample, the methods comprising a) adding a primer set comprising first and second primer pairs to the sample, the first primer pair having a first annealing temperature and the second primer pair having a second annealing temperature which is lower than the first annealing temperature, and the first primer pair defining a region of one of the target nucleic acid analytes, the second primer pair defining a region of another of the nucleic acid analytes; b) performing a thermocycling amplification reaction on the sample, the reaction comprising a set of temperature cycles comprising at least one temperature cycle having a minimum temperature which is both (i) not greater than the first annealing temperature, and (ii) greater than the second annealing temperature, the reaction further comprising at least one other temperature cycle having a minimum temperature which is not greater than the second annealing temperature; c) measuring a signal generated during the amplification reaction, thereby generating a kinetic signature from the measured signal; and d) comparing the kinetic signature to a reference signature, the reference signature corresponding with a signal generated when one or more of the plurality of target nucleic acid analytes is amplified in a sample comprising the primer set by a thermocycling reaction comprising at least one temperature cycle having a minimum temperature which is both (x) not greater than the first annealing temperature, and (y) greater than the second annealing temperature, the reaction further comprising at least one other temperature cycle having a minimum temperature which is not greater than the second annealing temperature, thereby making a determination as to the presence or absence of the at least two nucleic acid analytes.

In an aspect the present disclosure provides a method for detecting a nucleic acid analyte. The method comprises performing a nested asymmetric amplification reaction on a sample, measuring a signal generated during the nested asymmetric amplification reaction, and determining whether the analyte is present based on the signal. The nested asymmetric amplification reaction of the disclosure may comprise at least three nested primers, wherein at least one pair of primers of the at least three nested primer comprises a limiting primer and an excess primer. In some cases, the at least three nested primers bind to a single analyte. In some examples, the at least three nested primers may comprise at least two pairs of nested primers. In some further examples, the at least three nested primers comprise at least three pairs of nested primers. In some cases, the at least three nested primers may comprise at least two pairs of nested primers that bind to the same analyte. In some cases, the at least three pairs of nested primers may bind to the same analyte. The limiting primer may be present at an initial concentration of less than 1 µM. The excess primer may be present at an initial concentration of at least 2 times greater than the limiting primer. The limiting primer may have a concentration-adjusted melting temperature that is equal to or greater than the excess primer.

The method of the disclosure may detect the presence or absence of a plurality of the analytes in a sample. In some cases, the methods of the disclosure may detect the presence or absence of at least 1 analyte in a sample. The method of the disclosure may further comprise performing a melting curve analysis.

The signal may be signal that is an electromagnetic signal. For example, the signal may be a fluorescence emission signal. The signal may comprise intensity and a frequency. An analyte may be encoded by a signal intensity at a particular wavelength. An analyte may be also be encoded by a plurality of signal intensities at a plurality of wavelengths. The plurality of wavelengths may comprise at least three wavelengths. In some examples, the analyte may be encoded by at least one additional value selected from the group consisting of a value from the signal and a value from an additional signal. The least one additional value may be selected from the group consisting of a Förster resonance energy transfer (FRET) emission intensity, a FRET emission wavelength, an electrochemical signal, a chemiluminescence wavelength, a chemiluminescence intensity, a fluorescence bleaching rate, and a chemiluminescence bleaching rate. In some cases the at least one additional value is Förster resonance energy transfer (FRET) emission intensity.

The signal may be generated by a molecule that binds an amplification product. For example the signal may be generated by a hybridization probe. The hybridization probe may comprise a fluorophore and a quencher. The amplification reaction may comprise a plurality of hybridization probes that are specific for different analytes and comprise an identical fluorophore. In some examples, the number of the hybridization probes may be greater than the number of the analytes.

The signal generated by a single analyte may be plotted as a function of a variable selected from the group consisting of time and cycle number, thereby generating a plot. The plot may comprise at least two of the same regions selected from the group consisting of an exponential region, a linear region, and a plateau region. In some cases, both of the exponential regions occur over at least 4 cycles. In some cases, both of the exponential regions occur over at least 8 seconds. In some cases, both of the linear regions occur over at least 4 cycles. In some cases, both of the linear regions occur over at least 8 seconds. In some cases, both of the plateau regions occur over at least 4 cycles. In some cases, both of the plateau regions occur over at least 8 seconds.

The analyte may be selected from the group consisting of deoxyribonucleic acid (DNA) and ribonucleic acid (RNA). The methods of the disclosure may further comprise reverse transcribing an RNA. The analyte may be present at less than 1,000 copies. The sample may further comprise a reference analyte. The analyte may be from a source selected from the group consisting of an animal, a plant, a bacteria, a fungus, a parasite, and a virus. The animal may be human. In some cases, the analyte is from a source selected from the group consisting of human immunodeficiency virus, herpes simplex virus, human papilloma virus, *Plasmodium, Mycobacterium*, dengue virus, hepatitis virus, and influenza virus. In some other examples, the analyte is selected from the group consisting of human immunodeficiency virus polyprotease, human immunodeficiency virus p17, human papilloma virus E6, and human papilloma virus E7. The analyte may also be a nucleic acid variant. The analyte may be a nucleic acid encoding a 16S RNA sequence. The sample may be selected from the group consisting of a clinical sample, a food sample, an environmental sample, a pharmaceutical sample, and a sample from a consumer product.

The method of the disclosure may further comprise transforming a signal intensity into a frequency domain, thereby generating a transformed signal. The transforming may be performed by a method selected from the group consisting of a Fourier transform, a fast Fourier transform, a discrete Fourier transform, a discrete-time Fourier transform, and a wavelet transform. The method may further comprise comparing the transformed signal to a reference signal. The comparing may be used to determine if the analyte is present or absent.

The methods of the disclosure may be useful for unambiguously determining whether one or more analyte is present or absent. The methods of the disclosure may also comprise determining the initial amount of the analyte in the sample. The method of disclosure may further comprising making a clinical decision based on whether the analyte is present or absent. The clinical decision may comprise selection of an agent for administration to a subject in need thereof. The agent may be a therapeutic agent. The therapeutic agent may be selected from the group consisting of an antibiotic and an antiviral. The method the disclosure may further comprise transmitting information concerning the analyte through a computer network. The transmitting may be to a physician. In some examples, at least one step of the methods of the disclosure may be performed using instructions on a non-volatile computer readable medium. The instructions may be located on a remote server or on a thermal cycler.

The disclosure also provides a method of determining an amount of nucleic acid analyte. The method comprises performing an amplification reaction on a sample, measuring a signal generated during the amplification reaction, transforming the signal into a frequency domain thereby generating a transformed signal, comparing a value from the transformed signal to a value of reference signal, and determining the amount of the analyte based on the comparing. The transforming may be performed by a method selected from the group consisting of a Fourier Transform, a fast Fourier transform, a discrete Fourier transform, a discrete-time Fourier transform, and a wavelet transform. Transforming may be performed by an eigenbasis decomposition. The eigenbasis decomposition may be of a PCR curve. The eigenbasis decomposition may be of a characteristic PCR curve. The eigenbasis decomposition may comprise one or more eigenfunctions. The one or more eigenfunctions may comprise time-shifted, scaled sigmoidal, exponential, and/or linear curves corresponding to one or more primer sets. Transforming may be performed by an eigenbasis decomposition of a characteristic PCR curve comprising eigenfunctions consisting of time-shifted, scaled sigmoidal, exponential, and linear curves corresponding to specific primer-sets within a nested PCR amplification. The methods of the disclosure detect the presence or absence of a plurality of analytes. In some examples, each of the analytes produces a unique transformed signal amongst the analytes. The comparing may comprise comparing an intensity value at a particular frequency and time. In some cases, at least about 5 intensity values are generated during each cycle of the amplification reaction. The reference signal may be in a database of reference signals. The database may comprise at least 20 reference signals. The database may comprise at least 30 reference signals. The database may comprise at least 50 reference signals. The database may comprise less than 500 reference signals. The database may comprise less than 200 reference signals. The database may comprise less than 100 reference signals.

The disclosure also provides a kit for detecting a nucleic acid analyte. The kits of the disclosure comprise at least three nested primers. At least one pair of primers may comprise a limiting primer and an excess primer. The kit may also comprise a real time detection agent. The kit may detect the presence or absence of a plurality of analytes. At least one of the primers may be lyophilized. In some cases each of the primers is lyophilized. The kit may further comprise reagents for the detection of an amplified analyte. The reagents for the detection of an amplified analyte may comprise a fluorophore. The reagents for the detection of an amplified analyte may comprise a hybridization probe.

In some examples the at least three nested primers in the kit may bind to a single analyte. In some cases the at least three nested primers of the kit comprise at least two pairs of nested primers. The at least three nested primers may comprise at least three pairs of nested primers. In some further examples, the at least three nested primers comprise at least two pairs of nested primers that bind to the same analyte. In some cases the at least three nested primers comprise at least three pairs of nested primers that bind to the same analyte. The limiting primer may be present at an initial concentration of less than 1 µM. The excess primer may be present at an initial concentration of at least 2 times greater than the limiting primer. The limiting primer may have a concentration-adjusted melting temperature that is equal to or greater than the excess primer.

INCORPORATION BY REFERENCE

All publications and patent applications mentioned in this specification are herein incorporated in their entireties by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE INVENTION

I. General Overview

The present disclosure relates to methods, systems, compositions and kits relating to the detection and/or quantification of one or more analytes in a sample. The methods may be particularly useful for detection of a plurality of analytes in multiplexed reactions. Multiplexed reactions can permit performance of parallel reactions on the same sample, use of the same chamber to perform multiple reactions, and the ability to extract rich information from a sample in a fast and efficient manner. The methods disclosed herein may permit performance of multiplexed assays in a single solution. These methods can be used in place of or in addition to spectrally resolved fluorescence or chemiluminescence (e.g., PCR, ELISA), spatially resolved signals (e.g., microarrays, gel electrophoresis), temporally resolved signals (e.g., capillary electrophoresis), or combinations thereof (e.g., Sanger sequencing).

Specificity of the binding between PCR primers and template allows for selective amplification of intended targets. For instance, a typical quantitative polymerase chain reaction is run to "saturation," wherein the amplification reaction is run to the point at which at least one of the reactants such as primers, polymerase, probe, or free nucleotides is exhausted. When fluorescent reporters such as TaqMan probes, FRET probes, or intercalating dyes are used to interpret the extent of the DNA amplification, a fluorescence curve could be generated. The sigmoidal signature of a "saturation" fluorescence curve often occurs when the reporter probe concentrations are depleted at an ever-increasing rate.

However, this reaction (and by extension, its signature fluorescence) is limited by all reactant concentrations, including the PCR primers. As an example, when a single set of primers is used in equal concentrations, and when one primer is more efficiently extended than the other, the reaction becomes rate limited. This results in a linear, as compared to an exponential, amplification of DNA.

Generally, the methods of the disclosure comprise performing an amplification reaction, measuring a signal generated during the amplification reaction and determining the amount of the analytes present in the sample based on the measured signal. The method may additionally include transforming the measured signal to a second domain and comparing the transformed signal to a reference signal. The amount of the analyte present in the sample or the initial amount of analyte present in the sample may also be obtained based on the comparison of the transformed signal to the measured signal.

Figure 1:
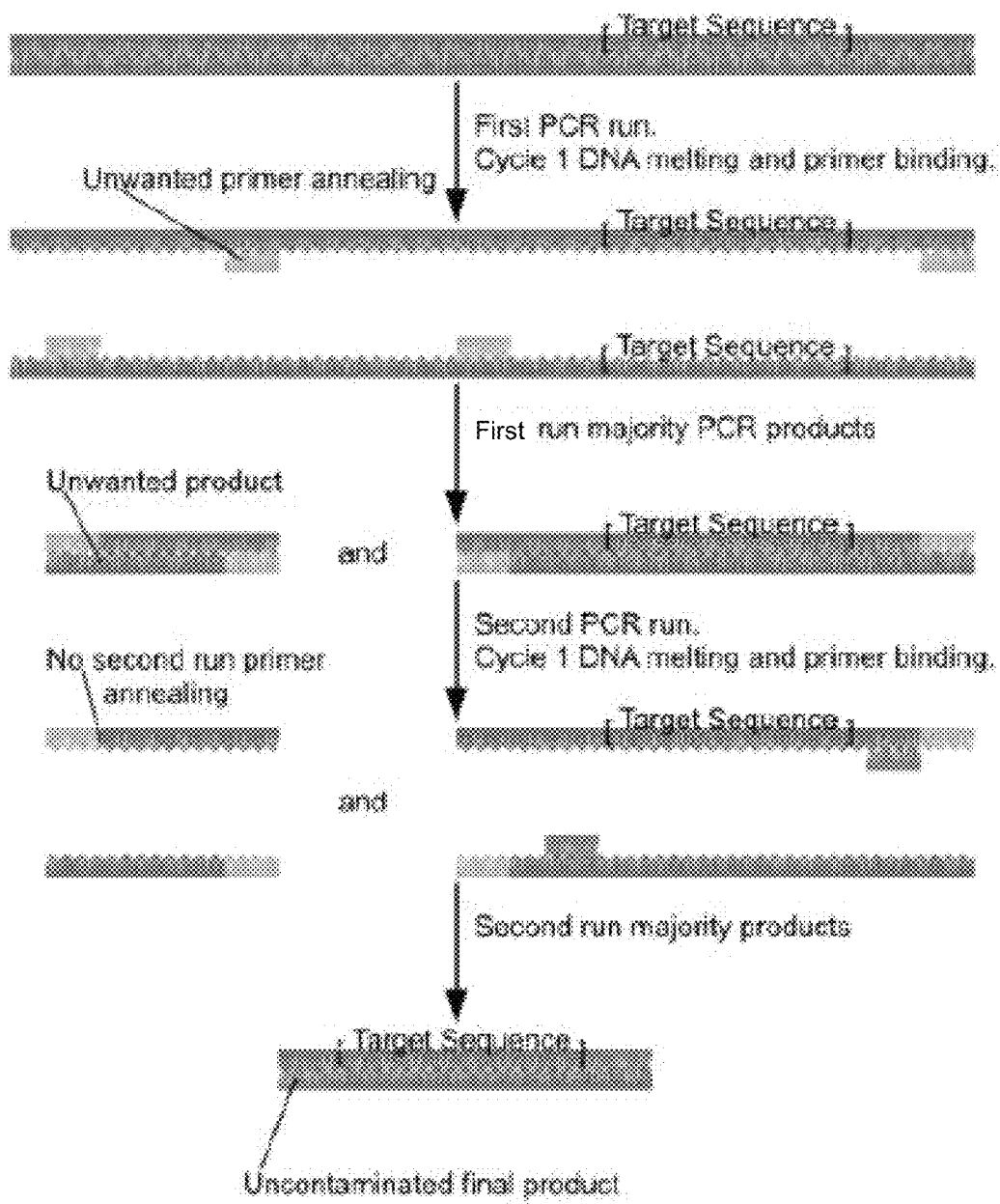
FIG. 1 shows a diagram illustrating the method of nested PCR.
Figure 2:
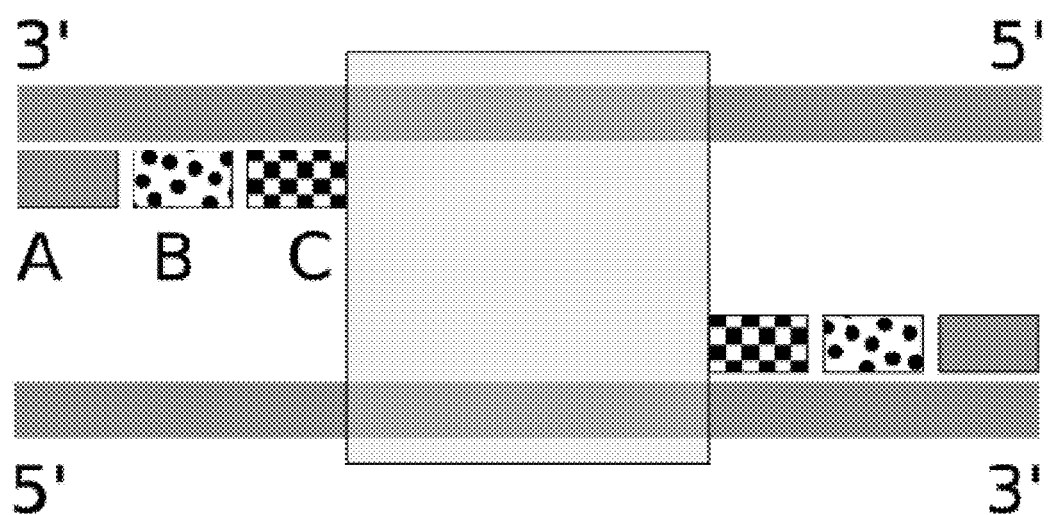
FIG. 2 shows a nested PCR with three primer pairs (A, B, C). The targeted area of interest is shown in the box.

A signal may be anything capable of measurement. For example, a signal may be a fluorescence signal. The amplification reaction for the methods of the disclosure may comprise semi-nested or nested PCR reactions. In these PCR reactions, at least two sets of primers are used in at least two successive reactions. In the first PCR reaction, one pair of primers is used. The products from the first PCR reactions are then used as template in a second PCR reaction, using one (semi-nested PCR reactions) or two different primers (nested PCR reactions). FIG. 1 shows a diagram illustrating the method of nested PCR and FIG. 2 shows a nested PCR with three primer pairs (A, B, C).

The amplification reactions of the disclosure are performed so as to generate characteristic signal curves that may be indicative of the presence and/or absence of one or more analytes. The characteristic curves may also be used to measure the amount of one or more analytes present in a sample. Such characteristic curves may be generated by varying (i) the number of primer pairs per target analyte, (ii) the primer sequences used for target analytes, and/or (iii) the ratio of the forward and the reverse primers in each primer pair.

Typically the amplification reactions of the disclosure are run such that either the forward or the reverse primer in each primer pair is rate limited. This may be done by adding each primer set such that there are different ratios of reverse and forward primers. For example, asymmetric PCR reactions, asymmetric nested PCR reactions, or asymmetric semi-nested PCR reactions may be used as amplification reactions in the methods of the disclosure. By choosing suitable ratios of the forward and the reverse primers, the amplification reactions of the disclosure may be tailored to generate curves that exhibit a characteristic linear amplification of the analytes. While this linear amplification may be non-ideal for efficient amplification of the target analytes, it may allow for discrimination of targets. Furthermore, tuning of primer concentration and the number of primers for a particular nested reaction allows for the engineering of a particular fluorescent signature for a given target. The fluorescent signal generated by an analyte may be plotted as a function of a variable selected from the group consisting of time and cycle number, thereby generating a plot or a characteristic curve. Preferably, the fluorescence signal is provided in AFU and is plotted against the number of cycles.

The characteristic curves generated by the methods of the disclosure may comprise one or more baseline regions, one or more exponential regions, one or more linear regions, and/or one or more plateau regions. In some cases the curves comprise at least two of the same regions selected from the group consisting of a baseline region, an exponential region, a linear region, and a plateau region. For example, the curves comprise one or more of at least two baseline regions, at least two exponential regions, at least two linear regions and/or at least two plateau regions. The amplification reactions of the disclosure may be conducted such that each target analyte in a sample generates a characteristic curve, which may indicate the presence or absence of the particular target analyte. A curve can be characterized by one or more of: (i) the number of baseline regions in a curve, (ii) the number of linear regions in a curve, (iii) the number of exponential regions in a curve, (iv) the number of plateau regions in a curve, (v) the slope of the one or more linear regions in a curve, (vi) the duration/length of one or more plateau regions in a curve, (vii) the duration/length of one or more linear regions in a curve, (viii) the duration/length of one or more exponential regions in a curve, (ix) the duration/length of one or more baseline regions in a curve, (x) the duration between two consecutive baseline regions in a curve, (xi) the duration between two consecutive exponential regions in a curve, (xii) the duration between two consecutive plateau regions in a curve, and/or (xiii) the duration between two consecutive linear regions in a curve. In some cases a curve is characterized by one or more of the preceding properties along with one or more additional properties not listed here. In some cases a curve is only characterized by one or more properties not listed here.

Figure 6:
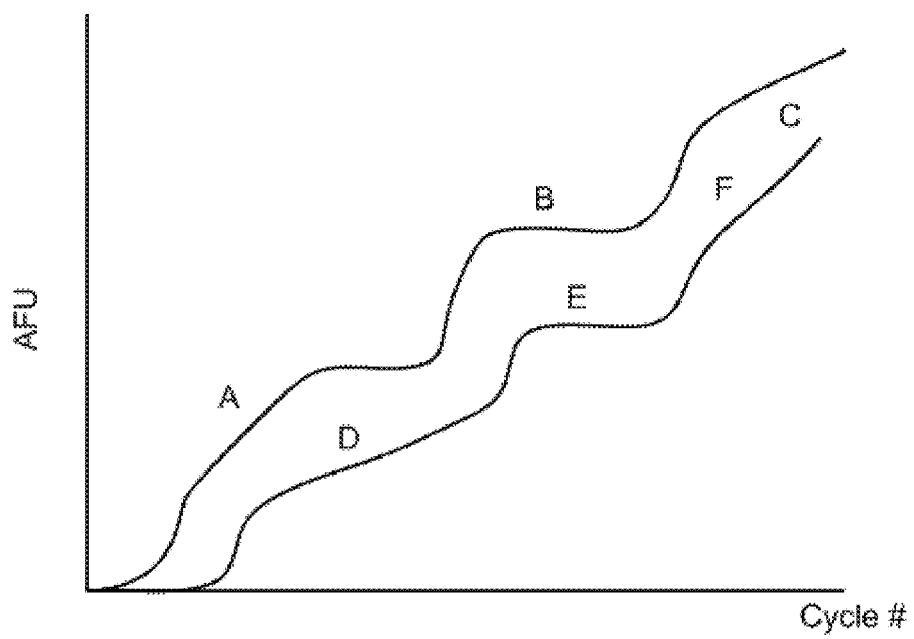
FIG. 6 shows the characteristic fluorescence curves (curve ABC and curve DEF) of two polymerase chain reactions.

Once the characteristic curves are generated, these curves may be analyzed by curve fitting algorithms. These algorithms may determine the number of baseline regions in a curve, the number of linear regions in a curve, the number of exponential regions in a curve, the number of plateau regions in a curve, the slope of the one or more linear regions in a curve, the duration/length of one or more plateau regions in the curve, the duration/length of one or more linear regions in the curve, the duration/length of one or more exponential regions in the curve, the duration/length of one or more baseline regions in the curve, the duration between two consecutive baseline regions in the curve, the duration between two consecutive exponential regions in the curve, the duration between two consecutive plateau regions in the curve, and/or the duration between two consecutive linear regions in the curve. Furthermore, if these curves are in superposition (e.g. more than one target is in a single, multiplexed reaction), each target can be uniquely identified if the curves are in the linear dynamic range of the fluorometer. For example, FIG. 6 shows two characteristic curves that may be generated from a sample comprising two target analytes by the methods of the disclosure.

The methods presented in this disclosure may be useful in a variety of applications. For example, the methods may be used to generate diagnostic data wherein these methods are employed to detect the presence or absence of one or more analytes that may be indicative of a disease or a condition. The methods are carried out such that each analyte, indicative of a disease, generates a characteristic curve. Exemplary diseases that may be diagnosed by the methods of the disclosure include cancer, autoimmune disease, cardio respiratory disease, liver disease, digestive disease, and so on.

In some cases, the methods may be used to detect infection with one or more pathogens. The methods provided herein may also be used to make a diagnosis and to make a clinical decision based on that diagnosis. For example, whether a particular target analyte is present or absent in a sample from an individual may assist in selection of an agent for administration into the subject. The agent is a therapeutic agent for example, antibiotic or antiviral agent. In some cases, the methods of the disclosure may indicate the presence of a bacterial polynucleotide in a sample taken from a subject, this may lead to the treatment of the subject by administering an antibiotic to the subject. In other cases, the methods of the disclosure may indicate the presence of a viral polynucleotide in a sample taken from a subject, this may lead to a clinical decision of administering an antiviral agent to the subject.

The methods may further be used to monitor the progress of a disease in an individual or to monitor the efficiency of a treatment method. Such methods include monitoring samples from the individual at regular time intervals and studying the changes in the characteristic curves generated by the corresponding one or more disease indicative analytes.

In other examples, the methods of the disclosure may also be used to identify genetic markers in an individual or a population of individuals. The genetic marker may be a molecular genetic marker, for example PCR based markers. Non-limiting examples of techniques that may be used for analysis of genetic markers by the methods of the disclosure include RAPD (random amplification of polymorphic DNA), SSRs (simple sequence repeats (SSR or microsatellite, or short tandem repeats)), SCAR (sequence characterized amplified region), AFLP (amplified fragment length polymorphism (AFLP)), SNP (single nucleotide polymorphism), CAPS (cleaved amplified polymorphic sequence), etc.).

II. Definitions

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of ±20% or ±10%, or ±5%, or even ±1% from the specified value, as such variations are appropriate for the disclosed compositions or to perform the disclosed methods.

Unless defined otherwise, all technical and scientific terms used herein have the same meaning as is commonly understood by one of skill in the art to which this invention belongs.

The term "annealing temperature" as used herein refers to the maximum temperature at which a nucleic acid anneals to a target nucleic acid under given conditions sufficient for extension of the primer to proceed. When used to refer to the annealing temperature of a primer pair, this term refers to the maximum temperature, under given conditions, at which each member of a primer pair anneals to its corresponding sequence of a target template or analyte to be amplified, sufficient for extension of the primer to proceed. Where, as is usual, each member of a pair binds to a separate sequence, on an opposite strand, of a target double-stranded nucleic acid, the "annealing temperature" is the temperature at which both members of the pair is bound to its complementary sequence. Where one member of the pair binds at a lower temperature than the other member, the annealing temperature of the pair will be that lower temperature. Thus, the term "annealing temperature" refers to the annealing temperature of the primer with a lower annealing temperature in a primer pair. The "annealing temperature" of a primer or primer pair may be below the melting temperature of the primer or primer pair. The "annealing temperature" may be lower than the "melting temperature" by any number of degrees Celsius, including, but not limited to 0.5° C., 1.0° C., 1.5° C., 2.0° C., 2.5° C., 3.0° C., 3.5° C., 4.0° C., 4.5° C., 5.0° C., 5.5° C., 6.0° C., 6.5° C., 7.0° C., 7.5° C., 8.0° C., 8.5° C., 9.0° C., 9.5° C., 10.0° C. In some embodiments, annealing temperatures recited herein are concentration-adjusted annealing temperatures.

The term "melting temperature" as used herein refers to the temperature at which half of a DNA or nucleic acid duplex becomes single-stranded. The term "primer melting temperature" refers to the temperature at which half of the primers associated with a nucleic acid analyte will dissociate.

As used herein, the term analyte encompasses a nucleic acid, a portion of a nucleic acid, an open reading frame, an exonic region, or an intronic region. The analyte may be present on a chromosome, a genome, a plasmid, or a cDNA. An analyte can be an overlapping nucleic acid sequence on the same strand of a chromosome or genome, for example.

As used herein, the term "temperature cycle" refers to the temperatures between which a sample is varied during a thermocycling amplification reaction. For example, in a standard thermocycling reaction, the sample might be repeatedly varied between an annealing temperature and a melting temperature. As used herein, each "temperature cycle" would comprise both the annealing and extension temperatures, as well as one or more temperature adjustment steps. As used herein, the term "n" refers to any positive integer.

III. Curve Signatures

Typically, the methods of the disclosure comprise plotting the fluorescent signal generated by an analyte as a function of a variable selected from the group consisting of time and cycle number, thereby generating a plot or a characteristic curve. Preferably, the fluorescence signal is provided in AFU and is plotted against cycle number. Often the AFU value may be normalized to a fixed proportional scale, for example to the scale of 0 to 100.

A typical fluorescent curve generated for a target analyte by the methods of the disclosure may comprise one or more baseline regions, plateau regions, linear regions and exponential regions. In some cases the curve comprises at least two of the same regions selected from the group consisting of a baseline region, an exponential region, a linear region, and a plateau region. As mentioned herein, a curve can be characterized by any one or more of the following properties: (i) the number of baseline regions in the curve, (ii) the number of linear regions in the curve, (iii) the number of exponential regions in the curve, (iv) the number of plateau regions in the curve, (v) the slope of the one or more linear regions in the curve, (vi) the duration/length of one or more plateau regions in the curve, (vii) the duration/length of one or more linear regions in the curve, (viii) the duration/length of one or more exponential region in the curve, (ix) the duration/length of one or more baseline regions in the curve, (x) the duration between two consecutive baseline regions in the curve, (xi) the duration between two consecutive exponential regions in the curve, (xii) the duration between two consecutive plateau regions in the curve, and/or (xiii) the duration between two consecutive linear regions in the curve. In some cases a curve is characterized by one or more of the preceding property along with one or more additional properties not listed here. In some cases a curve is characterized only by one or more properties not listed here.

In some cases the characteristic curves may differ in any one of the above listed properties. For example, the curves may differ in number of baseline regions; or the curves may differ in number of plateau regions; or the curves may differ in the number of exponential regions; or the curves may differ in the number of linear regions; or the curves may differ in slope of the one or more linear regions; or the curves may differ in duration/length of one or more plateau regions; or the curves may differ in duration/length of one or more linear regions; or the curves may differ in duration/length of one or more exponential regions; or the curves may differ in the duration of one or more baseline regions; or the curves may only differ in the duration between any two consecutive baseline regions of the curves; or the curves may differ in the duration between any two consecutive exponential regions of the curve; or the curves may differ in the duration between any two consecutive plateau regions of a curve; or the curves may only differ in the duration between any two consecutive linear regions of a curve. For example, a curve with one linear region may indicate the presence of first target analyte in a sample while another curve with two linear regions may indicate the presence of a second target analyte in a sample. In another example, a curve with a positive slope of the linear region may indicate the presence of first target analyte in a sample while another curve with a negative slope in the linear region may indicate the presence of a second target analyte in a sample.

In some cases the curves will differ in any two of the above listed properties. For example the curves may differ in number of plateau regions and the number of linear regions; or the curves may differ by the slope of one or more linear regions and the number of plateau regions; or the curves differ in the length/duration of one or more linear regions and the length/duration of one or more plateau region.

In other cases the curves will differ in any 3, 4, 5, 6, 7, 8, 9, 10, 11, or 12 of the above listed properties. In some cases the curves will differ in all 13 of these properties. In some cases the curves will differ in a combination of these properties plus one or more additional properties not listed here.

The number of baseline regions, plateaus, exponential regions, and the number of linear regions in a curve, indicative of a particular target analyte, may be varied by varying the number of nested primers used for a target analyte. If a single primer pair is used for a target analyte, the resulting curve will typically have a single baseline region, a single plateau, a single exponential region and a single linear region. As the number of nested primer pairs is increased to 2, 3, 4, etc. the number of baseline regions, plateaus, exponential regions, and the number of linear regions may increase correspondingly.

The characteristic curves may comprise 1, 2, 3, 4, 5, 6, 7, 8, 9, 10, or more baseline regions. For example the curve may comprise 15, 20, 25 or even more baseline regions. The characteristic curves may comprise 1, 2, 3, 4, 5, 6, 7, 8, 9, 10, or more plateau regions. For example the curve may comprise 15, 20, 25 or even more plateau regions. The characteristic curves may comprise 1, 2, 3, 4, 5, 6, 7, 8, 9, 10, or more exponential regions. For example the curve may comprise 15, 20, 25 or even more exponential regions. The characteristic curves may comprise 1, 2, 3, 4, 5, 6, 7, 8, 9, 10, or more linear regions. For example the curve may comprise 15, 20, 25 or even more linear regions.

In some case the characteristic curves will comprise equal number of baseline regions, plateau regions, exponential regions, and linear regions. For example, a characteristic curve may comprise 1 baseline region, 1 exponential region, 1 linear region and 1 plateau region. Similarly a characteristic curve may comprise 2 baseline regions, 2 exponential regions, 2 linear regions and 2 plateau regions. Alternatively characteristic curve may comprise 3 baseline regions, 3 exponential region, 3 linear regions and 3 plateau regions. A characteristic curve may also comprise 4, 5, 6, 7, 8, 9, 10 or more of each baseline regions, exponential regions, linear regions and plateau regions. For example the curve may comprise 15, 20, 25 or even more of each baseline regions, exponential regions, linear regions and plateau regions.

In some cases the characteristic curves will comprise different numbers of baseline regions, plateau regions, exponential regions, and linear regions. In some cases the characteristic curves will comprise equal number of baseline regions, plateau regions, and exponential regions but a different number of linear regions. In some cases the characteristic curves will comprise equal number of baseline regions, exponential regions, and linear regions but a different number of plateau regions. In some cases the characteristic curves will comprise equal number of baseline regions, plateau regions and linear regions but a different number of exponential regions. In some cases the characteristic curves will comprise equal numbers of plateau regions, exponential regions, and linear regions, but a different number of baseline regions.

The curves may vary in the length or the duration of one or more plateau regions. The length/duration of a plateau region in a curve can for example be at least 2 cycles, for example at least 3, 4, 5, 6, 7, 8, 9, 10, 15, 20, 25, 30, 35, 40, 45, 50, or 100 cycles. In some cases, the length or the duration of a plateau region will be at most 100 cycles, for example at most 50, 45, 40, 35, 30, 25, 20, 15, 10, 9, 8, 7, 6, 5, 4, 3, 2 or 1 cycle. In some cases the length/duration of a plateau region in a curve is calculated in the unit of time. In such cases, the length/duration of a plateau region in a curve can for example be at least 30 seconds, for example at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95 or 100 minutes. In some cases, the length or the duration of a plateau region will be at most 100 minutes, for example at most 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2 or 1 minute. Further multiple plateau regions of a curve may all have same or different length/duration.

Similarly, the curves may also vary in the length or duration of the linear regions. The length/duration of a linear region in a curve can for example be at least 2 cycles, for example at least 3, 4, 5, 6, 7, 8, 9, 10, 15, 20, 25, 30, 35, 40, 45, 50, or 100 cycles. In some cases, the length or the duration of a linear region will be at most 100 cycles, for example at most 50, 45, 40, 35, 30, 25, 20, 15, 10, 9, 8, 7, 6, 5, 4, 3, 2 or 1 cycle. In some cases the length/duration of a linear region in a curve is calculated in the unit of time. In such cases, the length/duration of a linear region in a curve can for example be at least 30 seconds, for example at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95 or 100 minutes. In some cases, the length or the duration of a linear region will be at most 100 minutes, for example at most 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2 or 1 minute. Multiple linear regions of a curve may all have same or different length/duration.

The curves may vary in the length or the duration of one or more baseline regions. The length/duration of a baseline region in a curve can for example be at least 2 cycles, for example at least 3, 4, 5, 6, 7, 8, 9, 10, 15, 20, 25, 30, 35, 40, 45, 50, or 100 cycles. In some cases, the length or the duration of a baseline region will be at most 100 cycles, for example at most 50, 45, 40, 35, 30, 25, 20, 15, 10, 9, 8, 7, 6, 5, 4, 3, 2 or 1 cycle. In some cases the length/duration of a baseline region in a curve is calculated in the unit of time.

In such cases, the length/duration of a baseline region in a curve can for example be at least 30 seconds, for example at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95 or 100 minutes. In some cases, the length or the duration of a baseline region will be at most 100 minutes, for example at most 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2 or 1 minute. Further multiple baseline regions of a curve may all have same or different length/duration.

The curves may vary in the length or the duration of one or more exponential regions. The length/duration of an exponential region in a curve can for example be at least 2 cycles, for example at least 3, 4, 5, 6, 7, 8, 9, 10, 15, 20, 25, 30, 35, 40, 45, 50, or 100 cycles. In some cases, the length or the duration of an exponential region will be at most 100 cycles, for example at most 50, 45, 40, 35, 30, 25, 20, 15, 10, 9, 8, 7, 6, 5, 4, 3, 2 or 1 cycle. In some cases the length/duration of an exponential region in a curve is calculated in the unit of time. In such cases, the length/duration of an exponential region in a curve can for example be at least 30 seconds, for example at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95 or 100 minutes. In some cases, the length or the duration of an exponential region will be at most 100 minutes, for example at most 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2 or 1 minute. Further multiple exponential regions of a curve may all have same or different length/duration.

The slope (or gradient) of a linear region in a curve may be varied by varying the ratio of the corresponding forward and reverse primers. The slope of one or more linear regions of the curves may have any value. Different linear regions of a curve may have same or different values. In some case some of the multiple linear regions a curve have same values. In other cases multiple linear regions will all have different values. In some case a few of the multiple linear regions will have same value while the other will have different values. The slope may be steep (for example, a steep incline or steep decline) or shallow (for example, a shallow incline or a shallow decline). The value of the slope of the linear regions of the curves may be either positive or negative. In some cases the slope is positive with a numerical value in the range of 0-0.01, 0-0.1, 0-1, 0-2, 1-3, 0-4, 0-5, 0-6, 0-7, 0-8, 0-9, 0-10, 0-20, 0-30, 0-40, 0-50, 0-60, 0-70, 0-80, 0-90, or 0-100. In some cases the slope is positive with a numerical value greater than 100, 200, 300, 400, 500, 600, 700, 800, 900 or 1000. In some cases a slope is negative with a numerical value in the range of 0-0.01, 0-0.1, 0-1, 0-2, 1-3, 0-4, 0-5, 0-6, 0-7, 0-8, 0-9, 0-10, 0-20, 0-30, 0-40, 0-50, 0-60, 0-70, 0-80, 0-90, or 0-100. In some cases the slope is negative with a numerical value greater than 100, 200, 300, 400, 500, 600, 700, 800, 900 or 1000.

The curves may vary in the duration between two consecutive exponential regions. In some cases two consecutive exponential regions of a curve are separated by at least 1 cycles, for example at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 10,000 cycles. In some cases, the occurrence of two consecutive exponential regions of a curve are separated by at most 10,000 cycles, for example at most 900, 800, 700, 600, 500, 400, 300, 200, 100, 90, 80, 70, 60, 50, 45, 40, 35, 30, 25, 20, 15, 10, 9, 8, 7, 6, 5, 4, 3, 2 or 1 cycle. In some cases two consecutive exponential regions of a curve are separated by at least 1 cycles, for example at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95 or 100 minutes. In some cases two consecutive exponential regions of a curve are separated by at most 100 minutes, for example at most 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2 or 1 minute. Further, if a curve comprises more than two exponential regions, each pair of consecutive exponential regions may be separated by a same or a different number of cycles.

The curves may vary in the duration between two consecutive baseline regions. In some cases two consecutive baseline regions of a curve are separated by at least 1 cycles, for example at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 10,000 cycles. In some cases, the occurrence of two consecutive baseline regions of a curve are separated by at most 10,000 cycles, for example at most 900, 800, 700, 600, 500, 400, 300, 200, 100, 90, 80, 70, 60, 50, 45, 40, 35, 30, 25, 20, 15, 10, 9, 8, 7, 6, 5, 4, 3, 2 or 1 cycle. In some cases two consecutive baseline regions of a curve are separated by at least 30 seconds, for example at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95 or 100 minutes. In some cases two consecutive baseline regions of a curve are separated by at most 100 minutes, for example at most 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2 or 1 minute. Further, if a curve comprises more than two baseline regions, each pair of consecutive baseline regions may be separated by a same or a different number of cycles.

The curves may vary in the duration between two consecutive plateau regions. In some cases two consecutive plateau regions of a curve are separated by at least 1 cycles, for example at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 10,000 cycles. In some cases, the occurrence of two consecutive plateau regions of a curve are separated by at most 10,000 cycles, for example at most 900, 800, 700, 600, 500, 400, 300, 200, 100, 90, 80, 70, 60, 50, 45, 40, 35, 30, 25, 20, 15, 10, 9, 8, 7, 6, 5, 4, 3, 2 or 1 cycle. In some cases two consecutive plateau regions of a curve are separated by at least 30 seconds, for example at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95 or 100 minutes. In some cases two consecutive plateau regions of a curve are separated by at most 100 minutes, for example at most 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2 or 1 minute. Further, if a curve comprises more than two plateau regions, each pair of consecutive plateau regions may be separated by a same or a different number of cycles.

The curves may vary in the duration between two consecutive linear regions. In some cases two consecutive linear regions of a curve are separated by at least 1 cycles, for example at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 10,000 cycles. In some cases, the occurrence of two consecutive linear regions of a curve are separated by at most 10,000 cycles, for example at most 900, 800, 700, 600, 500, 400, 300, 200, 100, 90, 80, 70, 60, 50, 45, 40, 35, 30, 25, 20, 15, 10, 9, 8, 7, 6, 5, 4, 3, 2 or 1 cycle. In some cases two consecutive linear regions of a curve are separated by at least 30 seconds, for example at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95 or 100 minutes. In some cases two consecutive linear regions of a curve are separated by at most 100 minutes, for example at most 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2 or 1 minute. Further, if a curve comprises more than two linear regions, each pair of consecutive linear regions may be separated by a same or a different number of cycles.

When the methods of the present disclosure are used with multiplexed PCR assay, the curves obtained may be a combination/addition of the component curves. This disclosure also provides methods of interpreting combined curves. For example, combination of linear regions of two or more curves will result in a linear region wherein the resulting slope is the sum of the individual slopes. This may allow two or more reactions to be coded and decoded by their slopes. Similarly, linear region of one curve and exponential region of another curve may combine to a signature that may neither be purely linear nor purely exponential. Such combination may be decoded by a mathematical fit to the experimental data to tell that both targets may be present and amplifying. Further, combining a plateau region of a curve with a linear region of another curve may produce a result that may bear uniquely decodable information about both, e.g. the slope may identify the latter, while the magnitude of the signal at the starting cycle of the combined region may help identify the plateau.

IV. Methods

The disclosure provides methods and materials for rapidly and simultaneously performing genotypic analysis for many genetic markers of an individual. The methods comprise obtaining a nucleic acid sample from the individual to be genotyped, subjecting the sample to the amplification methods disclosed herein to amplify segments containing the genetic markers to be examined, plotting the signal measured during the amplification reaction to generate characteristic curves, and determining the presence or absence of genetic markers in the sample based on the characteristic curves obtained. The amplification reactions may be conducted by contacting the sample with one or more nested primer pairs (for example, allele-specific primers). The number of nested primer pairs, the primer sequences and their concentrations may be adjusted so that each genetic marker may generate a characteristic signal curve. Accordingly, every genetic marker present in the nucleic acid sample of the individual will generate a characteristic curve. These methods may also be repeated for a large group of individuals to obtain a genetic profile of genetic markers in a population of individuals.

The disclosure also provides methods for the detection of one or more diseases in an individual. For example, the method may be used to detect specific mutations associated with the onset and progression of a disease. Non limiting examples of the diseases that may be detected by the methods of the disclosure include cancer, cystic fibrosis, heart diseases, and leukemia. Other diseases that may be detected by the methods of this disclosure include Achondroplasia, Adrenoleukodystrophy, X-Linked, Agammaglobulinemia, X-Linked, Alagille Syndrome, Alpha-Thalassemia X-Linked Mental Retardation Syndrome, Alzheimer Disease, Alzheimer Disease, Early-Onset Familial, Amyotrophic Lateral Sclerosis Overview, Androgen Insensitivity Syndrome, Angelman Syndrome, Ataxia Overview, Hereditary, Ataxia-Telangiectasia, Becker Muscular Dystrophy also The Dystrophinopathies), Beckwith-Wiedemann Syndrome, Beta-Thalassemia, Biotinidase Deficiency, Branchiootorenal Syndrome, BRCA1 and BRCA2 Hereditary Breast/Ovarian Cancer, Breast Cancer, CADASIL, Canavan Disease, Cancer, Charcot-Marie-Tooth Hereditary Neuropathy, Charcot-Marie-Tooth Neuropathy Type 1, Charcot-Marie-Tooth Neuropathy Type 2, Charcot-Marie-Tooth Neuropathy Type 4, Charcot-Marie-Tooth Neuropathy Type X, Cockayne Syndrome, Colon Cancer, Contractural Arachnodactyly, Congenital, Cranio synostosis Syndromes (FGFR-Related), Cystic Fibrosis, Cystinosis, Deafness and Hereditary Hearing Loss, DRPLA (Dentatorubral-Pallidoluysian Atrophy), DiGeorge Syndrome (also 22q1 1 Deletion Syndrome), Dilated Cardiomyopathy, X-Linked, Down Syndrome (Trisomy 21), Duchenne Muscular Dystrophy (also The Dystrophinopathies), Dystonia, Early-Onset Primary (DYT1), Dystrophinopathies, The, Ehlers-Danlos Syndrome, Kyphoscoliotic Form, Ehlers-Danlos Syndrome, Vascular Type, Epidermolysis Bullosa Simplex, Exostoses, Hereditary Multiple, Facioscapulohumeral Muscular Dystrophy, Factor V Leiden Thrombophilia, Familial Adenomatous Polyposis (FAP), Familial Mediterranean Fever, Fragile X Syndrome, Friedreich Ataxia, Frontotemporal Dementia with Parkinsonism-17, Galactosemia, Gaucher Disease, Hemochromatosis, Hereditary, Hemophilia A, Hemophilia B, Hemorrhagic Telangiectasia, Hereditary 55, Hearing Loss and Deafness, Nonsyndromic, DFNA (Connexin 26), Hearing Loss and Deafness, Nonsyndromic, DFNB 1 (Connexin 26), Hereditary Spastic Paraplegia, Hermansky-Pudlak Syndrome, Hexosaminidase A Deficiency (also Tay-Sachs), Huntington Disease, Hypochondroplasia, Ichthyosis, Congenital, Autosomal Recessive, Incontinentia Pigmenti, Kennedy Disease (also Spinal and Bulbar Muscular Atrophy), Krabbe Disease, Leber Hereditary Optic Neuropathy, Lesch-Nyhan Syndrome Leukemias, Li-Fraumeni Syndrome, Limb-Girdle Muscular Dystrophy, Lipoprotein Lipase Deficiency, Familial, Lissencephaly, Marfan Syndrome, MELAS (Mitochondrial Encephalomyopathy, Lactic Acidosis, and, Stroke-Like Episodes), Monosomies, Multiple Endocrine Neoplasia Type 2, Multiple Exostoses, Hereditary Muscular Dystrophy, Congenital, Myotonic Dystrophy, Nephrogenic Diabetes Insipidus, Neurofibromatosis 1, Neurofibromatosis 2, Neuropathy with Liability to Pressure Palsies, Hereditary, Niemann-Pick Disease Type C, Nijmegen Breakage Syndrome Norrie Disease, Oculocutaneous Albinism Type 1, Oculopharyngeal Muscular Dystrophy, Ovarian Cancer, Pallister-Hall Syndrome, Parkin Type of Juvenile Parkinson Disease, Pelizaeus-Merzbacher Disease, Pendred Syndrome, Peutz-Jeghers Syndrome Phenylalanine Hydroxylase Deficiency, Prader-Willi Syndrome, PROP 1-Related Combined Pituitary Hormone Deficiency (CPHD), Prostate Cancer, Retinitis Pigmentosa, Retinoblastoma, Rothmund-Thorns on Syndrome, Smith-Lemli-Opitz Syndrome, Spastic Paraplegia, Hereditary, Spinal and Bulbar Muscular Atrophy (also Kennedy Disease), Spinal Muscular Atrophy, Spinocerebellar Ataxia Type 1, Spinocerebellar Ataxia Type 2, Spinocerebellar Ataxia Type 3, Spinocerebellar Ataxia Type 6, Spinocerebellar Ataxia Type 7, Stickler Syndrome (Hereditary Arthroophthalmopathy), Tay-Sachs (also GM2 Gangliosidoses), Trisomies, Tuberous Sclerosis Complex, Usher Syndrome Type I, Usher Syndrome Type II, Velocardiofacial Syndrome (also 22q1 1 Deletion Syndrome), Von Hippel-Lindau Syndrome, Williams Syndrome, Wilson Disease, X-Linked Adreno leukodystrophy, X-Linked Agammaglobulinemia, X-Linked Dilated Cardiomyopathy (also The Dystrophinopathies), and X-Linked Hypotonic Facies Mental Retardation Syndrome. Methods, provided herein can also be applied to detect mutations during the course of therapeutic intervention in the treatment of disease that can decide the course and efficacy of a given treatment.

The methods may further be used to measure the efficacy of a treatment. In such cases samples from a patient will be monitored over a course of time for changes in the characteristic curves. Similarly, the methods described herein may be used to monitor the course of a disease.

The methods disclosed herein may be used with subjects at risk for developing a disease or disorder, subjects who may or may not have already been diagnosed with a disease or disorder and subjects undergoing treatment and/or therapies for a disease or disorder. The methods of the present disclosure can also be used to monitor or select a treatment regimen for a subject who has a disease or disorder.

The disclosure also provides methods for detecting the presence of one or more pathogens. In some cases, the methods may be used to determine the presence of one or more viruses, bacteria, or fungi. For example, the methods may be used for detection of DNA viruses, RNA viruses, retroviruses. In some cases the methods may be used to detect/quantify dsDNA viruses, ssDNA viruses, dsRNA viruses, (+)ssRNA viruses, (−)ssRNA viruses, ssRNA-RT viruses or dsDNA-RT viruses. The method may be used to detect/quantify gram-positive (for example, gram-positive cocci and gram-positive bacilli) and gram-negative (for example, gram-negative cocci and gram-negative bacilli). These methods may further include extracting cellular components of the target pathogens such as genomic DNA, ribosomal RNA, transfer RNA, or messenger RNA. In these methods, the presence of each pathogen in a sample will be indicated by the corresponding characteristic curve. Non limiting examples of pathogens that may be detected by the methods of the disclosure include HIV-1, hepatitis B and C, human papillomavirus, *chlamydia trachomatis, neisseria gonorrhoeae*, cytomegalovirus, influenza, *salmonella typhi*, west nile virus, adenovirus, *actinomyces*, and *mycobacterium tuberculosis*. The methods of the disclosure also enable the identification of GMO (genetic modified organisms).

The methods of the disclosure would also be useful in tracking the presence and/or progression of mutations in patients and related model organisms. In some cases the patients may be cancer patients and the methods of the disclosure may be used to obtain information about the presence or absence of drug-resistant mutations. Such information may be of clinical meaning and utility, for e.g. a KRAS mutation may indicate colorectal cancer, and a T790M mutation of EGFR may indicate lung cancer. Similarly, the methods of the invention may be used to track genetic information in a model organism or a population of model organisms as they are exposed to different experimental drugs in pharmaceutical research. In some cases the model organism may be a mouse or a rat.

The methods of the disclosure may also be employed in genetic retroactive studies of archival tissue cross-referenced with patient histories and outcomes and implemented medication regimens. Such studies may generate new insights both in epidemiology and in fundamental understanding of diseases, for example cancer. The methods disclosed herein further provide for a means of multiplexed expression analysis in biological samples, e.g. blood, saliva, cerebrospinal fluid, etc., which can have both fundamental and clinical utilities.

V. Amplification Reactions

A. Polymerase Chain Reaction (PCR)

Amplification refers to any process by which the copy number of a target sequence is increased. Methods for amplification of target polynucleotides are known in the art, and include without limitation, methods based on PCR. Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered.

In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing.

Methods of optimization are well known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adaptor fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 50, or more cycles. In some embodiments, amplification is performed following the fill-in reaction. Amplification can be performed before or after pooling of target polynucleotides from independent samples.

(i) Nested PCR Reactions

In the methods of the present disclosure PCR reaction may be carried out in a traditional fashion where one set of specific primers is chosen for a signal nucleic acid target. However, strategies may also be used to increase PCR target yield. For example the amplification reaction may conducted under nested PCR conditions, wherein at least two pairs of primers are used, that is, a pair of outer primers and a pair of inner primers. Each primer pair comprises a forward primer and a reverse primer. Conventional nested PCR procedures utilize two sequential amplification processes. Specifically, the two sequential amplification processes include a first amplification process comprising at least one amplification step for amplifying an extended target sequence, and a second, subsequent amplification process comprising at least one amplification step for amplifying an internal sequence from the product of the first amplification process, wherein the internal sequence may or may not overlap one of the ends of the extended sequence. Each amplification step of the first amplification process employs an outer primer set typically comprising a pair of outer primers. Similarly, each amplification step of the second amplification process employs an inner primer set typically comprising a pair of inner primers. FIG. 1 shows a diagram illustrating the methods of nested PCR reactions and FIG. 2 shows a nested PCR with three primer pairs (A, B, C). The targeted area on interest is shown in the box. As used herein, nested PCR reactions are also meant to include semi-nested or hemi-nested PCR reactions wherein at least one of the primers used in the second amplification process is same as in the first amplification process.

The nested PCR methods of the present disclosure may be performed using plurality of primers, for example at least 3 nested primers, at least 4 nested primers, at least 5 nested primers, at least 6 nested primers, at least 7 nested primers, at least 8 nested primers, at least 9 nested primers, at least 10 nested primers, at least 11 nested primers, at least 12 nested primers, at least 13 nested primers, at least 14 nested primers, or at least 15 nested primers. In some example the methods may employ more than 15 nested primers for example 20, 25, 30, 35 or even more nested primers. In some embodiments the nested PCR methods of the present disclosure may be performed using at most 35 nested primers, 30 nested primers, 25 nested primers, 20 nested primers, 15 nested primers, 14 nested primers, 13 nested primers, 12 nested primers, 11 nested primers, 10 nested primers, 9 nested primers, 8 nested primers, 7 nested primers, 6 nested primers, 5 nested primers, 4 nested primers, 3 nested primers or 2 nested primers. In some example the methods may 35, 30, 25, 20, 15, 14, 13, 12, 11, 10, 9, 8, 7, 6, 5, 4, 3, or 2 nested primers.

The plurality of primers may comprise at least 2 pairs of nested primers, at least 3 pairs of nested primers, at least 4 pairs of nested primers, at least 5 pairs of nested primes, at least 6 pairs of nested primers, at least 7 pairs of nested primers, at least 8 pairs of nested primers, at least 9 pairs of nested primers, at least 10 pairs of nested primers, at least 11 pairs of nested primers, at least 12 pairs of nested primers, at least 13 pairs of nested primers, at least 14 pairs of nested primers, at least 15 pairs of nested primers, at least 16 pairs of nested primers, at least 17 pairs of nested primers, at least 18 pairs of nested primers, at least 19 pairs of nested primers or at least 20 pairs of nested primers. In some embodiments the plurality of primers may comprise at most 20 pairs of nested primers, 19 pairs of nested primers, 18 pairs of nested primers, 17 pairs of nested primes, 16 pairs of nested primers, 15 pairs of nested primers, 14 pairs of nested primers, 13 pairs of nested primers, 12 pairs of nested primers, 11 pairs of nested primers, 10 pairs of nested primers, 9 pairs of nested primers, 8 pairs of nested primers, 7 pairs of nested primers, 6 pairs of nested primers, 5 pairs of nested primers, 4 pairs of nested primers, 3 pairs of nested primers, or 2 pairs of nested primers.

For instance, as shown in FIG. 2, three nested primer pairs A, B, and C may be used. In this case, all three primers are effective at amplifying the targeted area of interest. By choosing primer sequences carefully for binding energy, they may exhibit different melt temperatures. This will allow the reaction kinetics for each primer to be tuned as a function of temperature.

Figure 5:
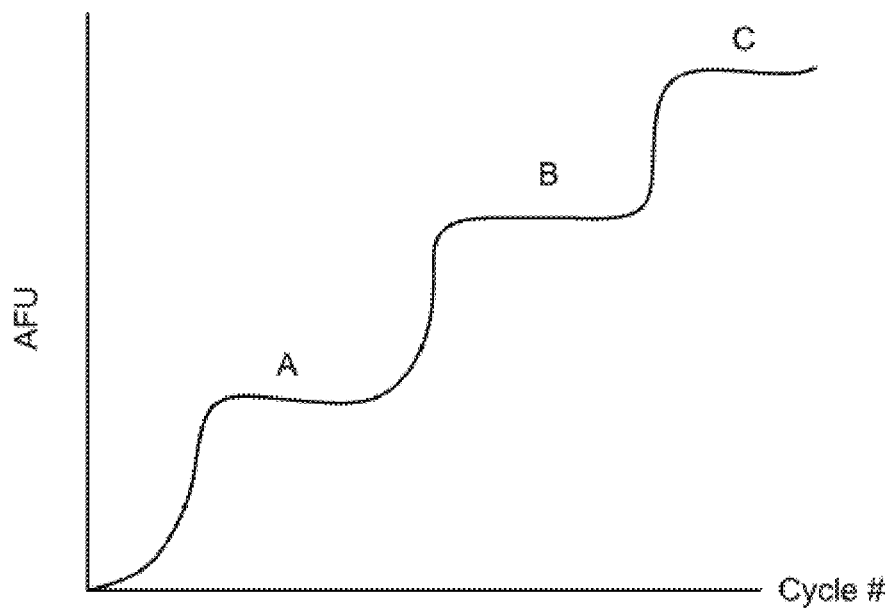
FIG. 5 shows the fluorescence curve of a nested, quantitative polymerase chain reaction.

By choosing the temperatures of the nested primer pairs, and by controlling the annealing temperature of the PCR amplification, the fluorescence signature of the amplification reaction may be tuned to generate multiple plateaus. For instance, as shown in FIG. 5, the three nested primer pairs from FIG. 2 may generate a unique fluorescence signature. Because the concentrations of primer sets A, B, and C may be carefully selected at the beginning of the reaction, the concentration of the nucleic acid target at plateaus A, B, and C may also be deterministic. This information may be used to select at which concentration of targets the linear PCR regions should be run.

(ii) Asymmetric PCR Reactions

Figure 3:
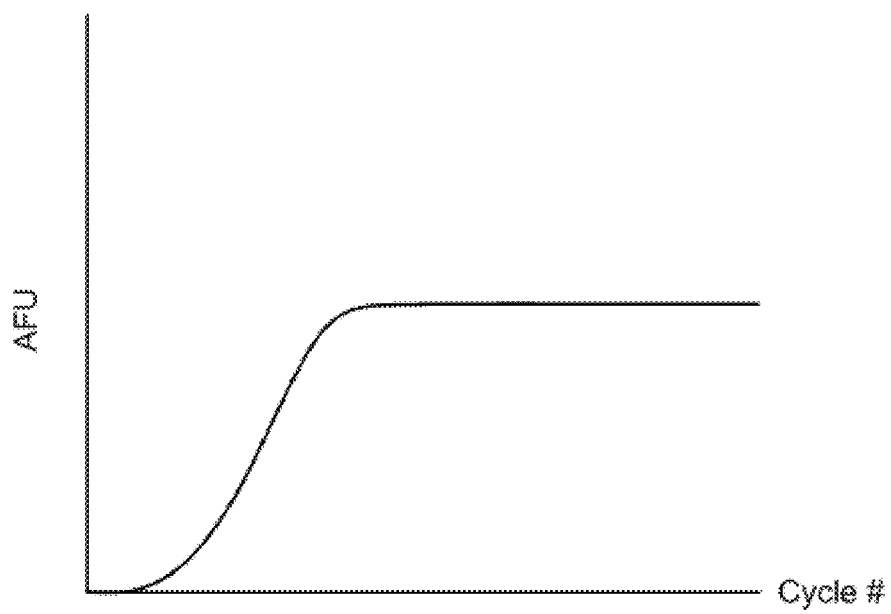
FIG. 3 shows the fluorescence curve of a saturated, quantitative polymerase chain reaction.
Figure 4:
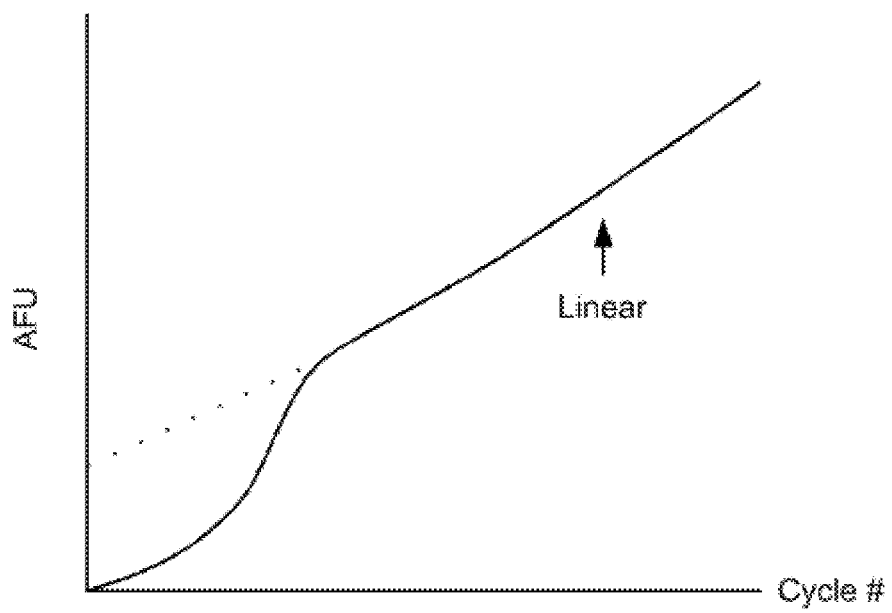
FIG. 4 shows the fluorescence curve of a biased-primer, quantitative polymerase chain reaction.

The nested PCR reactions of the present disclosure may further be run in such a way that either the forward or reverse primer in the nested primer pairs may be rate limited (asymmetric PCR conditions). This may be done by adding each primer set such that there are different ratios of reverse and forward primers. In some cases this may be done by titrating each primer set such that there are different ratios of reverse and forward primers. Accordingly, it may be possible to generate curves that exhibit a characteristic linear amplification of DNA. While this is linear amplification may be non-ideal for the efficient amplification of DNA, it may be suitable for the careful discrimination of DNA targets. FIG. 3 shows the fluorescence curve for a saturated, quantitative PCR reaction and FIG. 4 shows the fluorescence curve of an asymmetric (biased primer) quantitative PCR reaction. Furthermore, tuning of primer concentrations and the number of primers for a particular nested reaction may allow for the engineering of particular fluorescent signatures for a given target.

In certain embodiments, the starting molar concentration of the limiting primer is less than the starting molar concentration of the excess primer. The ratio of the starting concentrations of the excess primer and the limiting primer may be at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1, 1000:1 or more.

In certain embodiments, the starting molar concentration of the limiting primer is less than the starting molar concentration of the excess primer. The ratio of the starting concentrations of the excess primer and the limiting primer may be at most 1000:1, 950:1, 900:1, 850:1, 800:1, 750:1, 700:1, 650:1, 600:1, 550:1, 500:1, 450:1, 400:1, 350:1, 300:1, 250:1, 200:1, 150:1, 100:1, 95:1, 90:1, 85:1, 80:1, 75:1, 70:1, 65:1, 60:1, 55:1, 50:1, 45:1, 40:1, 35:1, 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1 or less.

In certain embodiments, the forward primer comprises a limiting primer and the reverse primer comprises an excess primer, wherein the excess primer is added to the combined sample at a concentration at least 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times 23 times, 24 times, 25 times, 30 times, 35 times, 40 times, 45 times, 50 times, 55 times, 60 times, 65 times, 70 times, 75 times, 80 times, 85 times, 90 times, 95 times, 100 times, 150 times, 200 times, 250 times, 300 times, 350 times, 400 times, 450 times, 500 times, 550 times, 600 times, 650 times, 700 times, 750 times, 800 times, 850 times, 900 times, 950 times, or 1000 times that of the limiting primer, and wherein the amplification conditions comprise asymmetric PCR conditions.

In certain embodiments, the forward primer comprises a limiting primer and the reverse primer comprises an excess primer, wherein the excess primer is added to the combined sample at a concentration at most 1000 times, 900 times, 950 times, 850 times, 800 times, 750 times, 700 times, 650 times, 600 times, 550 times, 500 times, 450 times, 400 times, 350 times, 300 times, 250 times, 200 times, 150 times, 100 times, 95 times, 90 times, 85 times, 80 times, 75 times, 70 times, 65 times, 60 times, 55 times, 50 times, 45 times, 40 times, 35 times, 30 times, 25 times, 24 times, 23 times, 22 times 21 times, 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, or 2 times that of the limiting primer, and wherein the amplification conditions comprise asymmetric PCR conditions.

In some embodiments, the forward primer comprises an excess primer and the reverse primer comprises a limiting primer, wherein the excess primer is added to the combined sample at a concentration at least 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times 23 times, 24 times, 25 times, 30 times, 35 times, 40 times, 45 times, 50 times, 55 times, 60 times, 65 times, 70 times, 75 times, 80 times, 85 times, 90 times, 95 times, 100 times, 150 times, 200 times, 250 times, 300 times, 350 times, 400 times, 450 times, 500 times, 550 times, 600 times, 650 times, 700 times, 750 times, 800 times, 850 times, 900 times, 950 times, or 1000 times that of the limiting primer, and wherein the amplification conditions comprise asymmetric PCR conditions.

In certain embodiments, the forward primer comprises an excess primer and the reverse primer comprises a limiting primer, wherein the excess primer is added to the combined sample at a concentration at most 1000 times, 900 times, 950 times, 850 times, 800 times, 750 times, 700 times, 650 times, 600 times, 550 times, 500 times, 450 times, 400 times, 350 times, 300 times, 250 times, 200 times, 150 times, 100 times, 95 times, 90 times, 85 times, 80 times, 75 times, 70 times, 65 times, 60 times, 55 times, 50 times, 45 times, 40 times, 35 times, 30 times, 25 times, 24 times, 23 times, 22 times 21 times, 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, or 2 times that of the limiting primer, and wherein the amplification conditions comprise asymmetric PCR conditions.

Primer length and sequence may be adjusted or modified, such that the concentration-adjusted melting temperature of the limiting primer at the start of the reaction is greater than or equal to the concentration-adjusted melting point of the excess primer. In some embodiments, the difference in the concentration-adjusted melting temperature of the limiting and the excess primer may be at least 0° C., 0.5° C., 1° C., 1.5° C., 2° C., 2.5° C., 3° C., 3.5° C., 4° C., 4.5° C., 5° C., 5.5° C., 6° C., 6.5° C., 7° C., 7.5° C., 8° C., 8.5° C., 9° C., 9.5° C., 10° C. or more. In some embodiments, the difference in the concentration-adjusted melting temperature of the limiting and the excess primer may be at most 10° C., 9.5° C., 9° C., 8.5° C., 8° C., 7.5° C., 7° C., 6.5° C., 6° C., 5.5° C., 5° C., 4.5° C., 4° C., 3.5° C., 3° C., 2.5° C., 2° C., 1.5° C., 1.0° C., 0.5° C., 0° C. or less.

Amplifications and assays according to embodiments of the present disclosure may be performed with initial reaction mixtures having ranges of concentrations of target molecules and primers. The methods may be used to assay samples containing less than 100 copies, 1000 copies, 10,000 copies, 20,000 copies, 30,000 copies, 40,000 copies, 50,000 copies, 60,000 copies, 70,000 copies, 80,000 copies, 90,000 copies, 100,000 copies, 200,000 copies, 300,000 copies, 400,000 copies, 500,000 copies, 600,000 copies, 70,000 copies, 800,000 copies, 900,000 copies or 1000,000 copies of the target analyte.

The methods may be used to assay samples containing more than 1000,000 copies, 900,000 copies, 800,000 copies, 700,000 copies, 600,000 copies, 500,000 copies, 400,000 copies, 300,000 copies, 200,000 copies, 100,000 copies, 90,000 copies, 80,000 copies, 70,000 copies, 60,000 copies, 50,000 copies, 40,000 copies, 30,000 copies, 20,000 copies, 10,000 copies, 1,000 copies or 100 copies of the target analyte.

The methods may be employed to assay sample comprising 0-100 copies, 0-1000 copies, 0-10,000 copies, 0-20,000 copies, 0-30,000 copies, 0-40,000 copies, 0-50,000 copies, 0-60,000 copies, 0-70,000 copies, 0-80,000 copies, 0-90,000 copies, 0-100,000 copies, 0-200,000 copies, 0-300,000 copies, 0-400,000 copies, 0-500,000 copies, 0-600,000 copies, 0-70,000 copies, 0-800,000 copies, 0-900,000 copies or 0-1000,000 copies of the target analyte.

The concentration of the limiting primer may range from a few to a several hundred nanomolars (nM). For example, the concentration of the limiting primer may be in the range of 1-50 nM, 1-100 nM, 1-150 nM, 1-200 nM, 1-250 nM, 1-300 nM, 1-350 nM, 1-400 nM, 1-450 nM, 1-500 nM, 50-100 nM, 50-150 nM, 50-200 nM, 50-250 nM, 50-300 nM, 50-350 nM, 50-400 nM, 50-450 nM, 50-500 nM, 100-150 nM, 100-200 nM, 100-250 nM, 100-300 nM, 100-350 nM, 100-400 nM, 100-450 nM, 100-500 nM, 150-200 nM, 150-250 nM, 150-300 nM, 150-350 nM, 150-400 nM, 150-450 nM, 150-500 nM, 200-250 nM, 200-300 nM, 200-350 nM, 200-400 nM, 200-450 nM, 200-500 nM, 250-300 nM, 250-350 nM, 250-400 nM, 250-450 nM, 250-500 nM, 300-350 nM, 300-400 nM, 300-450 nM, 300-500 nM, 350-400 nM, 350-450 nM, 350-500 nM, 400-450 nM, 400-500 nM, or 450-500 nM. Those of skill in the art appreciate that the concentration of the limiting primer may fall within any range bounded by any of these values.

In some examples the concentration of the limiting primer is less than 10 nM, 50 nM, 100 nM, 150 nM, 200 nM, 250 nM, 300 nM, 350 nM, 400 nM, 450 nM or 500 nM. In some examples the concentration of the limiting primer is greater than 10 nM, 50 nM, 100 nM, 150 nM, 200 nM, 250 nM, 300 nM, 350 nM, 400 nM, 450 nM or 500 nM.

The asymmetric nested PCR methods of the present disclosure include repeated thermal cycling through the steps of strand melting, primer annealing and primer extension. In a first-stage polymerase chain reaction, specific outer primers are added to the sample nucleic acid mixture, and the resulting mixture is subjected to an initial denaturation step to obtain single-stranded DNA templates. Following denaturation, the mixture is subjected to an initial annealing step, where the outer primers hybridize to opposite strands of the target nucleotide sequence. The temperature is then raised to allow for extension or replication of the specific segment of DNA across the region between the two primers by a thermostable DNA polymerase. The reaction is then thermocycled to allow for repeated denaturation, annealing, and extension, so that at each cycle, the amount of DNA representing the targeted nucleotide sequence between the two outer primers is doubled.

The first denaturation temperature may be in the range of 70-110° C., for example in the range of 70-75° C., 75-80° C., 80-85° C., 85-90° C., 90-95° C., 95-100° C., 100-105° C., or 105-110° C. The first annealing temperature is may be in the range of in the range of 35-65° C., for example in the range of 35-40° C., 40-45° C., 45-50° C., 50-55° C., 55-60° C., or 60-65° C. The first extension temperature may be in the range of in the range of 40-80° C., for example in the range of 40-45° C., 45-50° C., 50-55° C., 55-60° C., 60-65° C., 65-70° C., 70-75° C., or 75-80° C.

At the end of the first-stage polymerase chain reaction, the resulting mixture is carried over into a second-stage polymerase chain reaction. In this second-stage reaction, the products of the first-stage reaction are combined with specific inner primers. This mixture is again subjected to initial denaturation, annealing, and extension steps, followed by thermocycling as before to allow for repeated denaturation, annealing, and extension or the targeted nucleotide sequence.

The second denaturation temperature may be in the range of 70-110° C., for example in the range of 70-75° C., 75-80° C., 80-85° C., 85-90° C., 90-95° C., 95-100° C., 100-105° C., or 105-110° C. The second annealing temperature may be in the range of 35-65° C., for example in the range of 35-40° C., 40-45° C., 45-50° C., 50-55° C., 55-60° C., or 60-65° C. The second extension temperature may be in the range of in the range of 40-80° C., for example in the range of 40-45° C., 45-50° C., 50-55° C., 55-60° C., 60-65° C., 65-70° C., 70-75° C., or 75-80° C.

Other PCR techniques that can be used in the methods of the provided disclosure include, e.g., AFLP (amplified fragment length polymorphism) PCR (see e.g.: Vos et al. 1995. AFLP: a new technique for DNA fingerprinting. Nucleic Acids Research 23: 4407-14), allele-specific PCR (see e.g., Saiki R K, Bugawan T L, Horn G T, Mullis K B, Erlich H A (1986). Analysis of enzymatically amplified beta-globin and HLA-DQ alpha DNA with allele-specific oligonucleotide probes Nature 324: 163-166), Alu PCR, assembly PCR (see e.g., Stemmer W P, Crameri A, Ha K D, Brennan T M, Heyneker H L (1995). Single-step assembly of a gene and entire plasmid from large numbers of oligodeoxyribonucleotides Gene 164: 49-53), asymmetric colony PCR, helicase dependent PCR (see e.g., Myriam Vincent, Yan Xu and Huimin Kong (2004). Helicase-dependent isothermal DNA amplification EMBO reports 5 (8): 795-800), hot start PCR, inverse PCR (see e.g., Ochman H, Gerber A S, Hartl D L. Genetics. 1988 November; 120(3):621-3), in situ PCR, intersequence-specific PCR or IS SR PCR, digital PCR, linear-after-the-exponential-PCR or Late PCR (see e.g., Pierce K E and Wangh L T (2007). Linear-after-the-exponential polymerase chain reaction and allied technologies Real-time detection strategies for rapid, reliable diagnosis from single cells Methods Mol. Med. 132: 65-85), long PCR, nested PCR, real-time PCR, duplex PCR, multiplex PCR, quantitative PCR, or single cell PCR. Further examples of PCR techniques that may be used with the methods of the disclosure include, but are not limited to, quantitative PCR, quantitative fluorescent PCR (QF-PCR), multiplex fluorescent PCR (MF-PCR), real time PCR, reverse transcriptase PCR (RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. In some examples, the nested PCR reactions of the disclosure are conducted by having all primers added at the very beginning of PCR reaction and by programming the PCR machine to cycle among different sets of PCR temperatures over the course of the reaction, so that different sets of primers are activated in their respective phases only. For example, a nested PCR reaction may be carried out with three pairs of nested primers, say A, B, and C present at the same time. The reaction may be programmed in such a way that it runs for the first third of the cycles at hybridization temperature for the primers of sequence A, which is too high for the primers of B and C to hybridize. The second third of the cycles is then run at the temperature suitable for the primers of B but still too hot for hybridization of primer C. Finally, the final third of the cycles is run at temperature low enough for the primer pair C to hybridize. The lever of control in designing the methods of the disclosure include the sequence information and the programming of the temperatures and durations of the PCR cycles. The methods of the invention may in some cases involve varying the annealing and extension temperatures during the reaction, so that different primers get activated for extension at different times during the same PCR reaction.

In some cases, it may also be possible to program Taqman probes to activate at different times in the reaction as well. For example, the outer nesting primers may have annealing temperatures that are higher than the inner nested primers and the Taqman probe. This may mean that the Taqman probes may be protected from hydrolysis during the "pre-amplification", because while the template is being amplified, the probe is not hybridized and thus cannot be hydrolyzed. As a result no signal would be generated during the first stage of amplification, but when the inner pair of primers is engaged by lowering the annealing temperature, the probe would hybridize as well, and signal generation will be commenced. This characteristic may be used to keep the signal clean and help diagnose problems with the assay.

B. SPIA Amplification

Amplification of the analytes of interest employing a linear amplification method such as the single primer isothermal amplification (SPIA) can be used. SPIA enables generation of multiple copies of the strand specific sequence regions of interest and employs a single amplification primer, thus reducing the complexity associated with multiple oligonucleotide design and manufacturing, enables the use of a generic amplification primer, and can be linear.

Amplification by SPIA can occur under conditions permitting composite primer hybridization, primer extension by a DNA polymerase with strand displacement activity, cleavage of RNA from a RNA/DNA heteroduplex and strand displacement. In so far as the composite amplification primer hybridizes to the 3'-single-stranded portion (of the partially double stranded polynucleotide which is formed by cleaving RNA in the complex comprising a RNA/DNA partial heteroduplex) comprising, generally, the complement of at least a portion of the composite amplification primer sequence, composite primer hybridization may be under conditions permitting specific hybridization. In SPIA, all steps are isothermal (in the sense that thermal cycling is not required), although the temperatures for each of the steps may or may not be the same. It is understood that various other embodiments can be practiced given the general description provided above. For example, as described and exemplified herein, certain steps may be performed as temperature is changed (e.g., raised, or lowered).

Although generally only one composite amplification primer is described above, it is further understood that the SPIA amplification methods can be performed in the presence of two or more different first and/or second composite primers that randomly primer template polynucleotide. In addition, the amplification polynucleotide products of two or more separate amplification reactions conducted using two or more different first and/or second composite primers that randomly prime template polynucleotide can be combined.

The composite amplification primers are primers that are composed of RNA and DNA portions. In the amplification composite primer, both the RNA and the DNA portions are generally complementary and can hybridize to a sequence in the amplification-ready product to be copied or amplified. In some embodiments, a 3'-portion of the amplification composite primer is DNA and a 5'-portion of the composite amplification primer is RNA. The composite amplification primer is designed such that the primer is extended from the 3'-DNA portion to create a primer extension product. The 5'-RNA portion of this primer extension product in a RNA/DNA heteroduplex is susceptible to cleavage by RNase H, thus freeing a portion of the polynucleotide to the hybridization of an additional composite amplification primer. The extension of the amplification composite primer by a DNA polymerase with strand displacement activity releases the primer extension product from the original primer and creates another copy of the sequence of the polynucleotide. Repeated rounds of primer hybridization, primer extension with strand displacement DNA synthesis, and RNA cleavage create multiple copies of the strand-specific sequence of the polynucleotide.

In some embodiments, the composite amplification primer is generated in the amplification reaction mixture from a stem-loop chimeric pro-primer. The amplification reaction mixture can comprise a target partial duplex nucleic acid, for example a target partial duplex DNA, a chimeric stem-loop pro-primer, DNA polymerase with strand displacement activity, and an RNase targeting RNA in a RNA/DNA heteroduplex, for example RNase H. The RNA portion of the RNA/DNA heteroduplex at the stem of the chimeric stem-loop pro-primer can be cleaved by RNase H to generate, for example, a linear composite primer comprising a 3'-DNA and 5'-RNA. The linearized amplification primer can hybridize to a 3'-single stranded DNA portion (overhang) of a target partial duplex and can be extended by the DNA polymerase with strand displacement activity. The RNA portion of the hybridized primer in a heteroduplex can be cleaved by RNase H to free a portion of the primer binding site. A second linear composite amplification primer can hybridize to the freed primer binding site, and can be extended along the target DNA strand. The previously synthesized primer extension product (amplification product) can be displaced by the newly extended primer. Repeated cycles of primer hybridization, primer extension by strand displacement DNA polymerase, and cleavage of the RNA portion of the hybridized primer can generate multiple copies of a target nucleic acid.

C. Other Amplification Methods

Another method for amplification involves amplification of a single stranded polynucleotide using a single oligonucleotide primer. The single stranded polynucleotide that is to be amplified contains two non-contiguous sequences that are substantially or completely complementary to one another and, thus, are capable of hybridizing together to form a stem-loop structure. This single stranded polynucleotide already may be part of a polynucleotide analyte or may be created as the result of the presence of a polynucleotide analyte.

Another method for achieving the result of an amplification of nucleic acids is known as the ligase chain reaction (LCR). This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5'-tail comprising a promoter, a second DNA primer, reverse transcriptase, RNase-H, T7 RNA polymerase, NTP's and dNTP's.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTP's, and Q-beta-replicase.

Another method for amplifying nucleic acids is known as 3SR and is similar to NASBA except that the RNase-H activity is present in the reverse transcriptase. Amplification by 3SR is an RNA specific target method whereby RNA is amplified in an isothermal process combining promoter directed RNA polymerase, reverse transcriptase and RNase H with target RNA. See for example Fahy et al. PCR Methods Appl. 1:25-33 (1991).

Another method for amplifying nucleic acids is the Transcription Mediated Amplification (TMA) used by Gen-Probe. The method is similar to NASBA in utilizing two enzymes in a self-sustained sequence replication. See U.S. Pat. No. 5,299,491 herein incorporated by reference.

Another method for amplification of nucleic acids is Strand Displacement Amplification (SDA) (Westin et al 2000, Nature Biotechnology, 18, 199-202; Walker et al 1992, Nucleic Acids Research, 20, 7, 1691-1696), which is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Another method for amplification of nucleic acids is Rolling Circle Amplification (RCA) (Lizardi et al. 1998, Nature Genetics, 19:225-232). RCA can be used to amplify single stranded molecules in the form of circles of nucleic acids. In its simplest form, RCA involves the hybridization of a single primer to a circular nucleic acid. Extension of the primer by a DNA polymerase with strand displacement activity results in the production of multiple copies of the circular nucleic acid concatenated into a single DNA strand.

In some embodiments of the disclosure, RCA is coupled with ligation. For example, a single oligonucleotide can be used both for ligation and as the circular template for RCA. This type of polynucleotide can be referred to as a "padlock probe" or a "RCA probe." For a padlock probe, both termini of the oligonucleotide contain sequences complementary to a domain within a nucleic acid sequence of interest. The first end of the padlock probe is substantially complementary to a first domain on the nucleic acid sequence of interest, and the second end of the padlock probe is substantially complementary to a second domain, adjacent to the first domain near the first domain. Hybridization of the oligonucleotide to the target nucleic acid results in the formation of a hybridization complex. Ligation of the ends of the padlock probe results in the formation of a modified hybridization complex containing a circular polynucleotide. In some cases, prior to ligation, a polymerase can fill in the gap by extending one end of the padlock probe. The circular polynucleotide thus formed can serve as a template for RCA that, with the addition of a polymerase, results in the formation of an amplified product nucleic acid. The methods of the disclosure described herein can produce amplified products with defined sequences on both the 5'- and 3'-ends. Such amplified products can be used as padlock probes.

Some aspects of the disclosure utilize the linear amplification of nucleic acids or polynucleotides. Linear amplification generally refers to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some embodiments, amplification methods can be solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957 and Adessi et al., Nucleic Acids Research (2000): 28(20): E87) can be used. In some cases the methods of the disclosure can create a "polymerase colony technology," or "polony." referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003). The methods of the disclosure provide new methods for generating and using polonies.

Other suitable amplification methods include transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938. In some embodiments, amplification of target nucleic acids may occur on a bead. In other embodiments, amplification does not occur on a bead.

Multiplex Assays

In some embodiments, the present disclosure provides a multiplexed assay for simultaneous amplification, detection, and or/quantification of multiple target analytes in a sample. Multiplex assays or grammatical equivalents refer to the detection, analysis or amplification of more than one target analyte of interest in a single reaction mixture. In some embodiments the methods of the disclosure may be used to detect and/or quantify at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, 2000, 3000, or more different target analytes in a sample. In some embodiments the methods of the disclosure may be used to detect and/or quantify at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, 2000, 3000, or less different target analytes a sample. Accordingly, in some cases, the methods described herein may be used to simultaneously detect multiple diseases at once. In other cases the methods may be used to simultaneously detect multiple infectious agents in a sample. In some other cases the methods may be used to simultaneously detect multiple genetic markers in a sample.

In some embodiments the methods of the disclosure involve multiplexed PCR reactions. In some embodiments the methods may involve multiplexed nested PCR reactions or multiplexed asymmetric PCR reactions.

VI. Analytes

An analyte can be any molecule detectable by the methods provided herein. An analyte may be a polynucleotide, such as DNA, RNA, and any hybrid thereof, where the polynucleotide contains any combination of deoxyribo- and/or ribo-nucleotides. Polynucleotides may be single stranded or double stranded, as specified, or contain portions of both double stranded or single stranded sequence. Polynucleotides may contain any combination of nucleotides, including uracil, adenine, thymine, cytosine, guanine, inosine, xanthine, hypoxanthine, isocytosine, isoguanine and any nucleotide derivative thereof. As used herein, the term "nucleotide" may include nucleotides and nucleosides, as well as nucleoside and nucleotide analogs, and modified nucleotides, including both synthetic and naturally occurring species.

The analyte may comprise RNA. For example an analyte may comprise messenger RNA (mRNA), ribosomal RNA (rRNA), transfer RNA (tRNA), nuclear RNA (nRNA), small interfering RNA (siRNA), small nuclear RNA (snRNA), small nucleolar RNA (snoRNA), small Cajal body-specific RNA (scaRNA), microRNA (miRNA), double stranded (dsRNA), ribozyme, riboswitch 16SRNA or viral RNA. In some cases the methods of the invention may further comprise reverse transcription of the RNA analyte into its DNA complement (cDNA) through the use of reverse transcriptase. Subsequently, the cDNA may be amplified and assayed by the methods of the disclosure.

The analyte may comprise DNA, or complex DNA, for example genomic DNA. Analytes comprising genomic DNA may be obtained from any source and using any methods known in the art. Genomic DNA may be obtained from naturally occurring or genetically modified organisms or from artificially or synthetically created genomes. Genomic DNA may be isolated with or without amplification. Amplification may include PCR amplification, multiple displacement amplification (MDA), rolling circle amplification and other amplification methods. Genomic DNA may also be obtained by cloning or recombinant methods, such as those involving plasmids and artificial chromosomes or other conventional methods (see Sambrook and Russell, Molecular Cloning: A Laboratory Manual., cited supra.). The analyte may also comprise cDNA. The cDNA can be generated from RNA, e.g., mRNA. The DNA can be cDNA made from a mixture of genomes of different species. The DNA can be mitochondrial DNA (mtDNA). The DNA can be cell-free DNA. The cell-free DNA can be obtained from, e.g., a serum or plasma sample. The DNA can comprise one or more chromosomes. For example, if the DNA is from a human, the DNA can comprise one or more of chromosome 1, 2, 3, 4, 5, 6, 7, 8, 9, 10, 11, 12, 13, 14, 15, 16, 17, 18, 19, 20, 21, 22, X, or Y. The DNA can be from a linear or circular genome. The DNA can be plasmid DNA, cosmid DNA, bacterial artificial chromosome (BAC), or yeast artificial chromosome (YAC).

The DNA can be of a specific species, for example, human, rat, mouse, other animals, plants, bacteria, algae, viruses, and the like. The DNA can also be from a mixture of genomes of different species such as host-pathogen, bacterial populations and the like. The DNA can be from more than one individual or organism. The DNA can be double stranded or single stranded. The DNA can be part of chromatin. The DNA can be associated with histones. The methods described herein can be applied to high molecular weight DNA, such as is isolated from tissues or cell culture, for example, as well as highly degraded DNA, such as cell-free DNA from blood and urine and/or DNA extracted from formalin-fixed, paraffin-embedded tissues, for example.

An analyte may be a polynucleotide from a particular pathogen, such as a bacteria, virus, fungus, or helminth. For example, an analyte may be a polynucleotide from human immunodeficiency virus (HIV, for example human immunodeficiency virus p17), *Plasmodium*, herpes simplex virus, dengue virus, hepatitis virus, human papilloma virus (for example human papilloma virus E6 or human papilloma virus E7), influenza virus, *Mycobacterium*, Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae, *Streptococcus, Pseudomonas, Shigella, Campylobacter, Salmonella*, or *Escherichia*.

An analyte may also be encoding an enzyme, a protein or a polypeptide. The analyte may be indicative of presence and/or quantity of a carbohydrate, sugar, small molecule, a drug or metabolite (e.g., anti-cancer drug, chemotherapeutic drug, anti-viral drug, antibiotic drug, or any other molecule, such as a co-factor, receptor, receptor ligand, hormone, cytokine, blood factor, antigen, steroid, or antibody.

The samples may be derived from animals, plants, bacterias, fungi, parasites or viruses. In some cases, the samples are derived from humans. The different samples from which the analytes are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived there from, including, for example, cultured cell lines, biopsy, blood sample, or fluid sample containing a cell. Cells may comprise a specific cell type, such as a somatic cell, germline cell, wild-type cell, cancer or tumor cells, or diseased or infected cell. A cell may refer to a cell derived from a particular tissue or a particular locus in a target organism. A cell may comprise whole intact cells, or cell preparations. In some instances, samples may be obtained from bodily fluids which may include blood, urine, serum, lymph, saliva, mucosal secretions, perspiration, or semen. The subject may be an animal, including but not limited to, an animal such as a cow, a pig, a mouse, a rat, a chicken, a cat, a dog, etc., and is usually a mammal, such as a human.

Samples may also be obtained from manufactured products (such as cosmetics and foods), pharmaceutical products, or consumer products. In some instances, samples may be obtained from environmental samples including air, agricultural products, water, and soil. Samples can also be artificially derived, such as by chemical synthesis. In other instances samples may be the products of experimental manipulation including, recombinant cloning, polynucleotide amplification, polymerase chain reaction (PCR) amplification, purification methods (such as purification of genomic DNA or RNA), and synthesis reactions Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the methods of the disclosure, such as to remove excess or unwanted reagents, reactants, or products.

VII. Primers

According to the present disclosure, the term primer relates to a nucleic acid sequence, which is capable of hybridizing e.g. to the target nucleic acid sequence, to a nucleic acid sequence in the vicinity of the target sequence, or to a nucleic acid sequence overlapping with the target nucleic acid sequence. Alternatively, a primer may be capable of hybridizing to either the complementary sequence of the target nucleic acid sequence, to the complementary sequence of a nucleic acid sequence in the vicinity of the target nucleic acid sequence, or to the complementary sequence of a nucleic acid sequence overlapping with the target nucleic acid sequence.

The primers typically comprise oligonucleotides. The primers may comprise 5-50 nucleotides, for example 5-10 nucleotides, 5-15 nucleotides, 5-20 nucleotides, 5-25 nucleotides, 5-30 nucleotides, 5-35 nucleotides, 5-40 nucleotides, 5-45 nucleotides, 5-50 nucleotides, 10-15 nucleotides, 10-20 nucleotides, 10-25 nucleotides, 10-30 nucleotides, 10-35 nucleotides, 10-40 nucleotides, 10-45 nucleotides, 10-50 nucleotides, 15-20 nucleotides, 15-25 nucleotides, 15-30 nucleotides, 15-35 nucleotides, 15-40 nucleotides, 15-45 nucleotides, 15-50 nucleotides, 20-25 nucleotides, 20-30 nucleotides, 20-35 nucleotides, 20-40 nucleotides, 20-45 nucleotides, 20-50 nucleotides, 25-30 nucleotides, 25-35 nucleotides, 25-40 nucleotides, 25-45 nucleotides, 25-50 nucleotides, 30-35 nucleotides, 30-40 nucleotides, 30-45 nucleotides, 30-50 nucleotides, 35-40 nucleotides, 35-45 nucleotides, 35-50 nucleotides, 40-45 nucleotides, 40-50 nucleotides, or 45-50 nucleotides. In some embodiments the primers comprise 5, 10, 15, 20, 25, 30, 35, 40, 45 or 50 nucleotides. The primers may also comprise more than 50 nucleotides, for example 55, 60, 65, 70 or even more nucleotides.

A primer can be purified from a restriction digest by conventional methods, or it can be produced synthetically. The primer is preferably single-stranded for maximum efficiency in amplification, but the primer can be double-stranded. Double-stranded primers may denatured, i.e., treated to separate the strands. One method of denaturing double stranded nucleic acids is by heating.

The methods of designing and preparing primers that are appropriate for amplification reaction are well known to the person of ordinary skill in the art. Important features when designing oligonucleotides to be used as amplification primers include, but are not limited to, an appropriate size amplification product to facilitate detection (e.g., by electrophoresis), melting temperatures for the members of a pair of primers, and the length of each primer (i.e., the primers need to be long enough to anneal with sequence-specificity and to initiate synthesis but not so long that fidelity is reduced during oligonucleotide synthesis). The length of the amplification primers depends on several factors including the nucleotide sequence identity and the temperature at which these nucleic acids are hybridized or used during in vitro nucleic acid amplification. Primers can be designed using, for example, a computer program such as OLIGO (Molecular Biology Insights, Inc., Cascade, Colo.).

In some embodiments primers may include a detectable label, although a label may also be introduced by other means (for example via a labeled probe) during the amplification assay. In the former case, the labeled primer will result in a labeled amplification product, as the labeled primers are incorporated into the products. Labeled primers are available from commercial suppliers such as CPG, Inc. (Lincoln Park, N.J.), or they can be prepared via conjugating a label to an unlabeled primer. Labeling oligonucleotides such as primers can be carried out using conventional coupling procedures. Specific coupling procedures, however, will vary depending on the reactive group or groups present on the label and/or on the oligonucleotide. Preferred labels include those moieties detectable by spectroscopic, photochemical, biochemical, immunochemical, or chemical means. Such labels include, without limitation, fluorescence, chemiluminescence, dyes, biotin, haptens, enzymes, enzyme substrates, enzyme cofactors, enzyme inhibitors, enzyme subunits, metal ions, electron-dense reagents, and radioactive isotopes (e.g., 32P). The label moiety can be directly or indirectly attached to the primer.

For example, is primer is labeled at the 5' ends with a fluorophore, the amplified target sequence will be labeled with the detectable fluorescent material, and the intensity of fluorescence emitted from the fluorescent material may be measured using a fluorescence spectrophotometer. Suitable fluorophores that may be used with the primers of the disclosure include those described above. For example the primers may be labeled with 6-FAM; Alexa fluor 405, 430, 488, 532, 546, 555, 568, 594, 633, 647, or 660; Cy2; Cy3; Cy3.5; Cy5; Cy5.5; Cy7; hydroxycoumarin; methoxycoumarin; aminocoumarin; fluorescein; HEX; R-phycoerythrin; rhodamine Red-X; ROX; Red 613; Texas Red; allophycocyanin; TruRed; BODIPY 630/650; BODIPY 650/665; BODIPY-FL; BODIPY-R6G; BODIPY-TMR; BODIPY-TRX; carboxyfluorescein; Cascade Blue; 6-JOE; Lissamine rhodamine B; Oregon Green 488, 500, or 514; Pacific Blue; REG; Rhodamine Green; SpectrumAqua; TAMRA; TET; and Tetramethylrhodamine.

VIII Signals

The methods presented in this disclosure involve the measurement of a signal. The signal may comprise a intensity and/or a frequency. In many of the exemplary embodiments described in this disclosure, a fluorescent signal may be used. The fluorescent signal is often described as being measured in color (i.e., wavelength) and intensity. Color may be measured by using a spectrophotometer or by using a band pass filter that only allows light of a certain wavelength to reach a photodetector. Such band pass filters are commonly used in qPCR machines. Intensity is measured by using a photo detector. In some cases each analyte is encoded by a signal intensity at a particular wavelength. In some cases, each analyte is encoded by a plurality of signal intensities at a plurality of wavelengths. For example, each analyte may be labeled with a single intensity of 1, 2, 3, 4, 5 or more wavelengths. In some cases an analyte is encoded by at least one additional value selected from the group consisting of a value from said signal and a value from an additional signal. In some cases, the one additional value is selected from the group consisting of a Förster resonance energy transfer (FRET) emission intensity, a FRET emission wavelength, an electrochemical signal, a chemiluminescence wavelength, a chemiluminescence intensity, a fluorescence bleaching rate, and a chemiluminescence bleaching rate. For example, at least one additional value is Förster resonance energy transfer (FRET) emission intensity.

Although many of the exemplary embodiments described in this disclosure are described in terms of a fluorescent signal, this is by no means limiting. The methods provided in this disclosure may be used with any signal, for example Förster resonance energy transfer (FRET) emission intensity, a FRET emission wavelength, a chemiluminescent wavelength, a chemiluminescent intensity, a electromagnetic signal, a fluorescence bleaching rate, or a chemiluminescence bleaching rate.

Some of the methods provided in this disclosure utilize a reagent that generates a signal in the presence of an analyte. In some cases, these reagents are probes. The probes may be hybridization probes. The hybridization probes may be an oligonucleotide probe attached to a fluorophore and a quencher (e.g., a TAQMAN probe).

The methods of the disclosure may use one or more reagents or probes to detect the presence of each analyte. For example, 1, 2, 3, 4, 5, 6, 7, 8, 9, 10, 11, 12, or more reagents or probes may be used to detect the presence of an analyte. In some cases, at least 1, 2, 3, 4, 5, 6, 7, 8, 9, 10, 11, 12, or more reagents or probes may be used to detect the presence of an analyte. In some cases, fewer than 2, 3, 4, 5, 6, 7, 8, 9, 10, 11, 12, or more reagents or probes may be used to detect the presence of an analyte.

As described above, oligonucleotide probes attached to a fluorophore and a quencher may be used to detect the presence of an analyte in a polynucleotide amplification assay. So long as the quencher and the fluorophore are in proximity, the quencher quenches the fluorescence emitted by the fluorophore upon excitation by a light source. The sequence of the oligonucleotide probe is designed to be complementary to a polynucleotide sequence present in an analyte, and therefore capable of hybridizing to the polynucleotide sequence present in the analyte. Hybridization of the oligonucleotide probe may be performed in a nucleic acid amplification reaction comprising primers (e.g., a polymerase chain reaction). Upon extension of the primers by a DNA polymerase, the 5' to 3' exonuclease activity of the polymerase degrades the probe, releasing the fluorophore and the quencher into the medium. The proximity between the fluorophore and the quencher is broken and the signal from the fluorophore is no longer quenched. Thus, the amount of fluorescence detected is a function of the amount of analyte present. If no analyte is present, the probe will not hybridize to an analyte, and the fluorophore and quencher will remain in close proximity. Little or no signal will be produced.

Oligonucleotide probes may have one or a plurality of fluorophores and quenchers per probe. For example, in some embodiments an oligonucleotide probe may comprise 1, 2, 3, 4, 5, 6, 7, 8, 9, 10, or more fluorophores. An oligonucleotide probe may comprise at least 1, 2, 3, 4, 5, 6, 7, 8, 9, or 10 fluorophores. An oligonucleotide probe may comprise fewer than 2, 3, 4, 5, 6, 7, 8, 9, or 10 fluorophores. An oligonucleotide probe may comprise 1, 2, 3, 4, 5, 6, 7, 8, 9, 10, or more quenchers. An oligonucleotide probe may comprise at least 1, 2, 3, 4, 5, 6, 7, 8, 9, or 10 quenchers. An oligonucleotide probe may comprise fewer than 2, 3, 4, 5, 6, 7, 8, 9, or 10 quenchers. Attachment of probes and quenchers to a probe may be performed in the same reaction or in serial reactions. A series of reactions may be performed to label probes with at least one fluorophore and the reaction products may be mixed to generate a mixture of probes with different fluorophores.

Suitable fluorophores for use in the present disclosure include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, and others described in the 11th Edition of the Molecular Probes Handbook by Richard P. Haugland, hereby expressly incorporated by reference in its entirety.

Commercially available fluorescent nucleotide analogues readily incorporated into the labeling oligonucleotides include, for example, Cy3-dCTP, Cy3-dUTP, Cy5-dCTP, Cy5-dUTP (GE Healthcare), fluorescein-12-dUTP, tetramethylrhodamine-6-dUTP, Texas Red®-5-dUTP, Cascade Blue®-7-dUTP, BODIPY® FL-14-dUTP, BODIPY®R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-1 4-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-1 4-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, and Alexa Fluor® 546-1 4-UTP (Invitrogen).

Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Invitrogen), and Cy2, Cy3.5, Cy5.5, and Cy7 (GE Healthcare).

If an oligonucleotide probe comprises two or more fluorophores, these fluorophores may be arranged to allow Förster (Fluorescence) resonance energy transfer (FRET) to occur between the fluorophores. Briefly, FRET is a mechanism of energy transfer between fluorophores. Using FRET-based probes allows one excitation source to generate two different fluorescence emission signals by excitation of a single fluorophore. For example, the methods described herein may used paired probes, where one probe in the pair is attached to a fluorophore and a quencher and a second probe is attached to two fluorophores (in close enough proximity for FRET to occur) and a quencher. Any combination of fluorophores and quenchers that provide for FRET may be used. Such an approach doubles the number of fluorescent probes that may be used with an excitation source, because a single excitation source can be used to produce two signals: one from the probe with one fluorophore and one from the probe with two fluorophores in close enough proximity to provide for FRET. For example, using the encoding method described in Table 8, the number of unambiguously detectable analytes could be increased from 16 to 32 by pairing each of the probes in Table 8 with a corresponding FRET probe.

In one example, a first probe may be labeled with the fluorophore 5'-fluorescein amidite (5'-FAM) and the quencher black hole quencher 1 (BHQ-1). A second probe may be labeled with 5'-FAM in close proximity (e.g., attached to) to cyanine 5.5 (Cy5.5) and the quencher black hole quencher 3 (BHQ-3). Upon digestion of the probe, via the nuclease activity of the polymerase, two fluorescent signals are generated from a single excitation wavelength (e.g., 470 nm). The fluorophore from the first probe will fluoresce at about 520 nm. The fluorophores on the second probe undergo FRET. The donor fluorophore, FAM is excited by the excitation light source (e.g., 470 nm) and transfers its energy to the acceptor fluorophore, Cy5.5. The acceptor fluorophore emits at about 705 nm. These fluorophores and quenchers are merely exemplary. Any fluorophores that can undergo FRET and any quenchers that can quench fluorescence are suitable for use with the disclosure. Methods for producing FRET-based probes are described in Jothikumar et al., BioTechniques, 2009, 46(7):519-524.

Although many aspects of the disclosure are exemplified using nucleic acid-based probes, one of ordinary skill in the art will readily recognize that other forms of probes would work equally well with the disclosure described in this disclosure. For example, a binding molecule specific to an analyte could be used as a probe. Non-limiting exemplary binding molecules include an antibody recognizing an analyte, and generating a signal in the presence of an analyte.

Similarly, although many aspects of the disclosure are exemplified using fluorescent labels attached to probes, many other types of labels could also be used with the methods of the disclosure. The disclosure can be used with any label capable of generating a measurable signal.

For multicolor imaging, signals of different wavelength can be obtained by multiple acquisitions or by simultaneous acquisition by splitting the signal, using RGB detectors or analyzing the whole spectrum (Richard Levenson, Cambridge Healthtech Institutes, Fifth Annual meeting on Advances in Assays, Molecular Labels, Signaling and Detection, May 17-18th Washington D.C.). Several spectral lines can be acquired by the use of a filter wheel or a monochrometer. Electronic tunable filters such as acoustic-optic tunable filters or liquid crystal tunable filters can be used to obtain multispectral imaging (e.g. Oleg Hait, Sergey Smirnov and Chieu D. Tran, 2001, Analytical Chemistry 73: 732-739). An alternative method to obtain a spectrum is hyperspectral imaging (Schultz et al., 2001, Cytometry 43:239-247).

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, 7,689,022 and in WO99/47964, each of which also is hereby incorporated by reference in its entirety for all purposes. The fluorophores that may be used with the disclosure are not limited to any of the fluorophores described herein. For example, fluorophores with improved properties are continually developed, and these fluorophores could readily be used with the methods provided in this disclosure. Such improved fluorophores include quantum dots, which may emit energy at different wavelengths after being excited at a single wavelength. The advantage of using such fluorophores is that only a single excitation source is needed, but many different signals may be quantified, for example in terms of color and intensity.

IX. Other Additives

The PCR reagents may furthermore comprise additives such as a DNA polymerase (e.g. Taq polymerase), deoxynucleotide triphosphates (e.g. dATP, dCTP, dTTP, and dGTP), salts (e.g. KCl and MgCl2), buffer (e.g. Tris-HCl), biopreservatives (e.g. sodium azide), PCR enhancers (e.g. Betaine, Trehalose, etc.), and inhibitors (e.g. RNAse inhibitors), detergents (e.g. Triton X-100, Triton X-114, NP-40, Tween 20, Tween 80 and similar non ionic detergents). Other additives may include 2-pyrrolidone, acetamide, N-methylpyrolidone (NMP), B-hydroxyethylpyrrolidone (HEP), propionamide, NN-dimethylacetamide (DMA), N-methylformamide (MMP), NN-dimethylformamide (DMF), formamide, N-methylacetamide (MMA), dimethyl sulfoxide (DMSO), polyethylene glycol, betaine, tetramethylammonium chloride (TMAC), 7-deaza-2'-deoxyguanosine, T4 gene 32 protein, 2-mercaptoethanol or glycerol. Paragraph 104 and 105 remove MIP 00187 for polymerase; 00188 for different types of PCR X. Analysis of the Characteristic Curves Once characteristic curves are generated for a set of reaction, these curves can be analyzed by curve-fitting algorithms. The curves may be fitted using, for example, linear regression, non-linear regression (for example Levenberg-Marquardt (LM) method), or may simply connect fluorescence data from adjacent cycles with a smoothed or non-smoothed line. The fitted curves may be then used to determine the slope of the amplification reaction in its linear regime. In the embodiments where two or more of these curves are in superposition (i.e. where two or more targets are present in multiplexed fashion) each target may be uniquely identified as long as the curves are in the linear dynamic range of the fluorometer. The multiplexed discrimination of multiple targets in a single reaction by means of reaction rates allows for another axis of orthogonality for PCR multiplexing.

In some cases the curves generated by the methods of the disclosure may be analyzed by taking the derivative of the signal with respect to cycle number and generating a derivative plot. In the derivative plot, the plateaus will show up as zeros or near-zeros. The normal saturating amplification will show up as a sinusoidal-like peak between two zeros. The linear amplification will shows up as plateaus, where the magnitude will informative of the slope and will be proportional to the concentration of respective primer.

Another strategy for discriminating curves is to transform them into a transform domain thereby generating a transformed signal. For example, the signal may be transformed into a frequency domain. The transforming may be performed by any suitable method including Fourier transform, fast Fourier transform (FFT), discrete time Fourier transform (DTFT), discrete time Fourier transform (DTFT), short-time Fourier transform, fractional Fourier transform, chirplet transforms, or wavelet transform. In general, any eigenvalue transformation that is a conformal map can be used to extract the natural frequencies of the PCR curve. Once this is obtained, the frequency space signature (FIG. 7) of each reaction can be used to resolve which targets were present. Careful design of the primers and probes will allow reaction rate information to be resolved as well, allowing for a built-in gauge of the quality or efficiency of the PCR reaction. Furthermore, this frequency space signature can be cross-correlated against a database of known target combinations to determine the most likely mix of targets in a particular reaction.

Accordingly, in another aspect the disclosure provides a method of detecting a nucleic acid analyte in a sample. The method comprises performing an amplification reaction on a sample, measuring a signal generated during said amplification reaction, transforming the signal into a transform domain thereby generating a transformed signal, comparing the transformed signal to a reference signal, and based on the comparison determining whether the analyte is present or absent.

The reference signal may be a signal in a database of reference signals. The database may comprise at least 1, 5, 10, 50, 100, 200, 300, 400, 500 or more signals. In some cases, the database comprises at most 500, 400, 300, 200, 100, 50, 10, 5 or 1 signal.

XI. Kits

In one aspect, the disclosure provides kits containing any one or more of the elements disclosed in the above methods and compositions. In some embodiments, a kit comprises a composition of the disclosure, in one or more containers. The kits may further comprise additional agents, such as those described above, for use according to the methods of the disclosure. The kit elements may be provided in any suitable container, including but not limited to test tubes, vials, flasks, bottles, ampules, syringes, or the like.

An exemplary kit of the disclosure may comprise at least three nested primers, at least one pair of primers comprising a limiting primer and an excess primer, and a real time detection agent. The kits may further comprise one or more PCR reagents, for example salts, deoxynucleotide triphosphates, buffers, detergents, PCR inhibitors, PCR enhancers and nucleic acid polymerases. The kit may also comprise additives such as 2-mercaptoethanol, 2-pyrrolidone, acetamide, N-methylpyrolidone (NMP), B-hydroxyethylpyrrolidone (HEP), propionamide, NN-dimethylacetamide (DMA), N-methylformamide (MMP), NN-dimethylformamide (DMF), formamide, N-methylacetamide (MMA), dimethyl sulfoxide (DMSO), polyethylene glycol, betaine, tetramethylammonium chloride (TMAC), 7-deaza-2'-deoxyguanosine, T4 gene 32 protein, or glycerol. A kit may additionally include instructions for employing the kit components as well the use of any other reagent not included in the kit. Instructions can include variations that can be implemented.

The containers of the kits can generally include at least one vial, test tube, flask, bottle, syringe or other containers, into which a component may be placed, and preferably, suitably aliquoted. Where there is more than one component in the kit, the kit also can generally contain a second, third or other additional container into which the additional components can be separately placed. However, various combinations of components can be comprised in a container.

When the components of the kit are provided in one or more liquid solutions, the liquid solution can be an aqueous solution. However, the components of the kit can be provided as dried powder(s). Agents may be provided in aliquots for single-use or as stocks from which multiple uses, such as in a number of reaction, may be obtained. When reagents and/or components are provided as a dry powder, the powder can be reconstituted by the addition of a suitable solvent. Elements of the kit can further be provided, without limitation, in any suitable amounts and/or using any of the combinations (such as in the same kit or same container) described above or any other suitable combination known in the art.

The agents may be provided in a form that may be directly used in the methods of the disclosure, or in a form that requires preparation prior to use, such as in the reconstitution of lyophilized agents. For example, primers in kits provided herein may be in a lyophilized or non-lyophilized state. In some embodiments at least one primer provided in the kits is lyophilized. In some cases more than one, for example two, three, four, five, six or even more of the primers provided in a kit are in lyophilized state. In some examples, all of the primers contained in the kits of the present disclosure are lyophilized.

In certain embodiments, the concentration of the excess primer in the kits is at least 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times 23 times, 24 times, 25 times, 30 times, 35 times, 40 times, 45 times, 50 times, 55 times, 60 times, 65 times, 70 times, 75 times, 80 times, 85 times, 90 times, 95 times, 100 times, 150 times, 200 times, 250 times, 300 times, 350 times, 400 times, 450 times, 500 times, 550 times, 600 times, 650 times, 700 times, 750 times, 800 times, 850 times, 900 times, 950 times, or 1000 times that of the limiting primer.

In certain embodiments, the concentration of the excess primer in the kits is at most 1000 times, 900 times, 950 times, 850 times, 800 times, 750 times, 700 times, 650 times, 600 times, 550 times, 500 times, 450 times, 400 times, 350 times, 300 times, 250 times, 200 times, 150 times, 100 times, 95 times, 90 times, 85 times, 80 times, 75 times, 70 times, 65 times, 60 times, 55 times, 50 times, 45 times, 40 times, 35 times, 30 times, 25 times, 24 times, 23 times, 22 times 21 times, 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, or 2 times that of the limiting primer The length and sequence of the primes in the kits may be adjusted or modified such that the concentration-adjusted melting temperature of the limiting Primer is greater than or equal to the concentration-adjusted melting point of the excess primer. For example, the difference in the concentration-adjusted melting temperature of the limiting and the excess primer may be at least 0° C., 1° C., 1.5° C., 2° C., 2.5° C., 3° C., 3.5° C., 4° C., 4.5° C., 5° C., 5.5° C., 6° C., 6.5° C., 7° C., 7.5° C., 8° C., 8.5° C., 9° C., 9.5° C., 10° C. or more. In some embodiments, the difference in the concentration-adjusted melting temperature of the limiting and the excess primer may be at least 10° C., 9.5° C., 9° C., 8.5° C., 8° C., 7.5° C., 7° C., 6.5° C., 6° C., 5.5° C., 5° C., 4.5° C., 4° C., 3.5° C., 3° C., 2.5° C., 2° C., 1.5° C., 1° C., 0° C. or less.

The initial concentration of the limiting primers in the kits may be less than 500 nM. For example the initial concentration of the limiting primer may be less than 10 nM, 50 nM, 100 nM, 150 nM, 200 nM, 250 nM, 300 nM, 350 nM, 400 nM, 450 nM or 500 nM. In some embodiments the initial concentration of the limiting primers in the kits may be more than 500 nM. For example the initial concentration of the limiting primer may be more than 500 nM, 450 nM, 400 nM, 350 nM, 300 nM, 250 nM, 200 nM, 150 nM, 100 nM, 50 nM or 10 nM.

The at least one real time detection agent in the kits provided herein may be any reagent that generates a signal in the presence of an analyte. In some cases, these reagents are probes. The probes may be hybridization probes. The hybridization probes may be an oligonucleotide probe attached to a fluorophore and a quencher (e.g., a TAQMAN probe).

The kits may be for detection of pathogens, such as bacteria, virus, fungus, or helminth. For example, the kits provided herein may be used for detection of human immunodeficiency virus, *Plasmodium*, herpes simplex virus, dengue virus, hepatitis virus, human papilloma virus, influenza virus, *Mycobacterium*, Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae, *Streptococcus, Pseudomonas, Shigella, Campylobacter, Salmonella, Neisseria gonorrhoeae*, or *Escherichia*.

XII. Analytical Techniques and Instrumentation

The methods provided herein are suitable for use with a variety of detection methods. For example, the methods may be applied using an analytical technique that measures the wavelength and intensity of a fluorescent signal. This may be accomplished by measuring the intensity of a signal across a spectrum of wavelengths, or by using band pass filters that restrict the passage of certain wavelengths of light, thereby allowing only light of certain wavelengths to reach a photodetector. Many real-time PCR and quantitative PCR instruments comprise an excitation light source and band pass filters that enable the detection of fluorescent signals in four colors (e.g., blue, green, yellow, and red). Therefore, the methods of the disclosure can be readily applied using instruments widely used in the art.

The methods are also compatible with end point PCR and digital PCR methods. Digital PCR methods (e.g., DROPLET DIGITAL (BIORAD) and DYNAMIC ARRAY (FLUIDIGM)) produce highly sensitive quantification of polynucleotide copy numbers. The methods provided herein can be easily integrated into these systems to drastically expand their throughput by allowing multiplexing in a droplet or a dynamic array.

In some cases, instruments may be modified or constructed, for example, to provide additional excitation light sources, at multiple wavelength, and/or to provide additional band pass filters or a capability of determining a complete spectrum. Including additional excitation sources would allow for the excitation of a larger variety of fluorophores. Including additional band pass filters, or modifying or constructing an instrument capable of determining an entire spectrum allows detection of a wider variety of emissions from fluorophores. These techniques can be used to increase the number of fluorophores that can be used with the methods described in this disclosure and, accordingly, to increase the number of analytes that be simultaneously detected.

XIII. Systems and Software

The methods of this disclosure may also be performed as part of a system. For example, one or more steps of the methods described herein may be performed by software contained on a computer readable medium. The software may be used to convert measurements made on an instrument (e.g., a PCR machine) into the presence or absence of an analyte. The software may be used to calculate the slopes of the linear region of the generated characteristic curves. The software may also be used to transform the measured signal into a transform domain and to thereby generate a transformed signal. The software may compare the transformed signal to a reference signal and based on the comparison determine the amount of analyte present in the sample. In some cases the determined amount of the analyte in the sample may be used to conclude whether a said analyte is present or absent in the sample.

In one example, the software is embedded in the instrument making the measurement. In another example, the software is installed on a computer attached to the instrument making the measurement. In another example, the software is in the "cloud"—i.e., on a computer that another computer may communicate with through a network. Each of these elements may be connected to a controller that communicates with each of the elements and coordinates their actions. For example, a controller may initiate the measurement of the signal and generation of characteristic curves. The controller can execute software to transform the signal into a transform domain, thereby generating a transformed signal. The controller may also initiate the comparison of the measured signal or the transformed signal to a reference signal.

Alternatively, the controller may operate an oligonucleotide synthesis instrument that can synthesize the appropriate probes. After analysis of the sample on the instrument (which may also be automated), the controller can process the results of the analysis using the reference signal values. The controller may then provide these results to a user.

Figure 8:
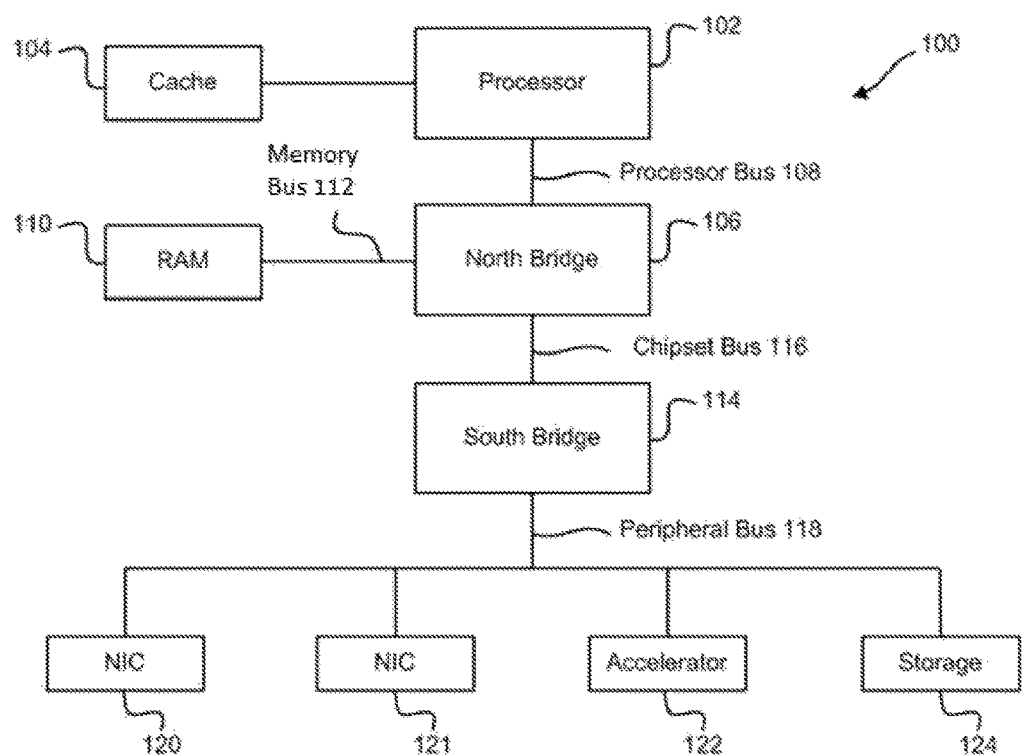
FIG. 8 shows a block diagram illustrating a first example architecture of a computer system that can be used in connection with example embodiments of the present disclosure.

FIG. 8 is a block diagram illustrating an example architecture of a computer system 100 that can be used in connection with example embodiments of the present disclosure. As depicted in FIG. 8, the example computer system can include a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 8, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 9:
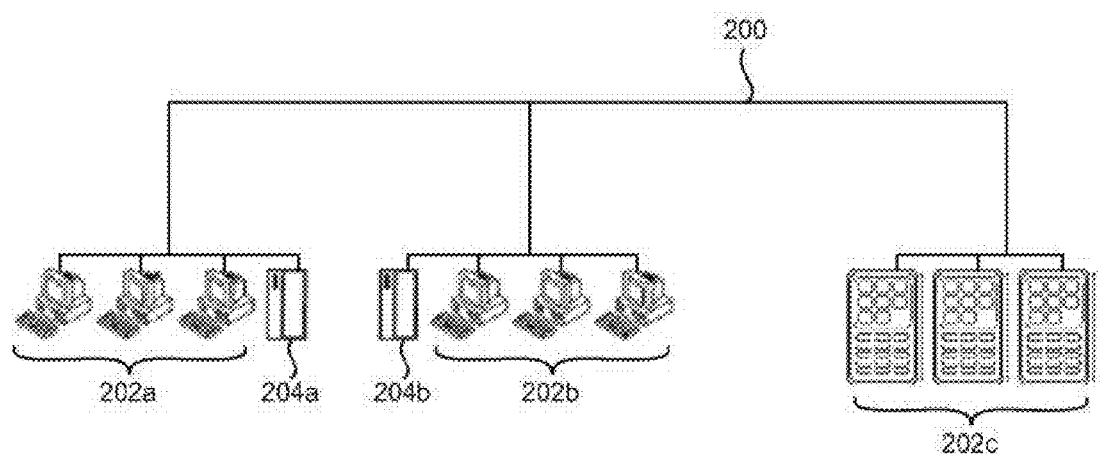
FIG. 9 shows a diagram illustrating a computer network that can be used in connection with example embodiments of the present disclosure.

FIG. 9 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 9 illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 10:
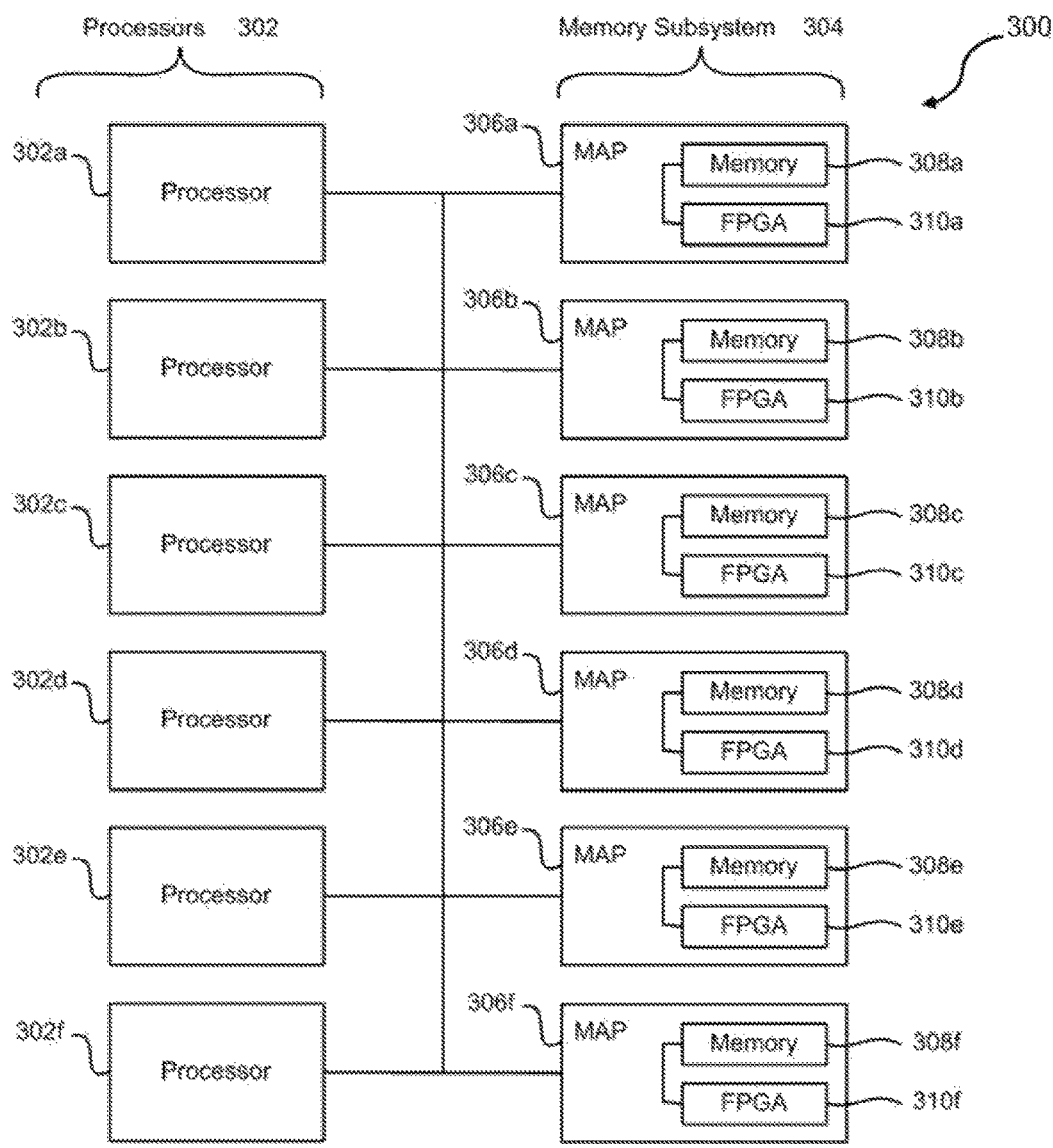
FIG. 10 shows a block diagram illustrating a second example architecture of a computer system that can be used in connection with example embodiments of the present disclosure.

FIG. 10 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 10, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 8.

XIV. Services

The methods provided herein may also be performed as a service. For example, a service provider may obtain the identity of a series of analytes that a customer wishes to analyze. The service provider may then encode each analyte to be detected by any of the methods described herein and provide appropriate reagents to the customer for the assay. The customer may perform the assay and provide the results to the service provider for decoding. The service provider may then provide the decoded results to the customer. The customer may also encode analytes, generate probes, and/or decode results by interacting with software installed locally (at the customer's location) or remotely (e.g., on a server reachable through a network). Exemplary customers include clinical laboratories, physicians, manufacturers, and the like.

EXAMPLES

Example 1

General Materials & Methods

1. DNA Sequences, Primers, and Probes

Synthesis of the oligonucleotides for the following examples is done by INTEGRATED DNA TECHNOLOGIES (Coralville, Iowa). HSV-1 and HSV-2 sequences from the Los Alamos National Laboratory reference sequence are selected for the exemplary study.

The 198-mer HSV-2 oligonucleotide is reconstituted with TE buffer at a concentration of 1.7 µM. Forward and reverse primers A for the HSV-2 oligonucleotide are reconstituted with TE buffer at a concentration of 100 µM and 1 µM respectively. Forward and reverse primers B for the HSV-2 oligonucleotide are reconstituted with TE buffer at a concentration of 40 µM and 1 µM respectively. Forward and reverse primers C for the HSV-2 oligonucleotide are reconstituted with TE buffer at a concentration of 3 µM and 1 µM respectively. A TAQMAN sense probe ("HSV-2probe1") is synthesized with a 6-FAM fluorophore at the 5' end and a BHQ-1 quencher at the 3' end.

The 199-mer HSV-1 oligonucleotide is reconstituted with TE buffer at a concentration of 1.5 µM. Forward and reverse primers D for the HSV-1 oligonucleotide are reconstituted with TE buffer at a concentration of 1 µM and 100 µM respectively. Forward and reverse primers E for the HSV-1 oligonucleotide are reconstituted with TE buffer at a concentration of 1 µM and 40 µM respectively. Forward and reverse primers F for the HSV-1 oligonucleotide are reconstituted with TE buffer at a concentration of 1 µM and 3 µM respectively. A TAQMAN sense probe ("HSV-1_probe1") is synthesized with a 6-FAM fluorophore at the 5' end and a BHQ-1 quencher at the 3' end. An additional TAQMAN sense probe ("HSV-1_probe2") is synthesized with Cy3 at the 5' end and BHQ-2 at the 3' end.

2. Polymerase Chain Reactions

All PCR reactions are performed in a ROCHE 480 LIGHTCYCLER instrument. Forty-five thermal cycles are performed, with a 60 second hot-start at 95° C. The cycling conditions for denaturation, annealing, and extension are 45 seconds, 50 seconds, and 60 seconds at 95° C., 65° C., and 70° C., respectively. Each experiment is run in quintuplicate, with a reaction volume of 15 µL. Fluorescence measurements are obtained in the following channels after every annealing step: 483 nm to 533 nm (FAM), 523 nm to 568 nm (Cy3), 558 nm to 610 nm (ROX), and 615 nm to 670 nm (Cy5).

Example 2

Detection of Polynucleotide Markers from Pathogens

This example describes the detection of polynucleotides from HSV-1 and HSV-2.

1. PCR Reaction Components

Three PCR reactions are assembled, using the reagents described in Table 1.

TABLE 1

Reagents for the three PCR reactions.

| Reaction No. | Type of Reagent | Reagent | Concentration | Volume |
|---|---|---|---|---|
| 1 | | UltraPure Water | — | 34 µL |
| | | Taq 5x Master Mix | — | 42 µL |
| | Template | HSV-2 Template | 17 nM | 2 µL |
| | Primers | HSV-2 FWD Primer A | 100 nM | 2 µL |
| | | HSV-2 RVS Primer A | 1 nM | 2 µL |
| | | HSV-2 FWD Primer B | 40 nM | 2 µL |
| | | HSV-2 RVS Primer B | 1 nM | 2 µL |
| | | HSV-2 FWD Primer C | 3 nM | 2 µL |
| | | HSV-2 RVS Primer C | 1 nM | 2 µL |
| | Probe | HSV-2 Probe 1 | 1 nM | 2 µL |

TABLE 1-continued

Reagents for the three PCR reactions.

| Reaction No. | Type of Reagent | Reagent | Concentration | Volume |
|---|---|---|---|---|
| 2 | | UltraPure Water | — | 34 µL |
| | | Taq 5x Master Mix | — | 42 µL |
| | Template | HSV-1 Template | 17 nM | 2 µL |
| | Primers | HSV-1 FWD Primer D | 1 nM | 2 µL |
| | | HSV-1 RVS Primer D | 100 nM | 2 µL |
| | | HSV-1 FWD Primer E | 1 nM | 2 µL |
| | | HSV-1 RVS Primer E | 40 nM | 2 µL |
| | | HSV-1 FWD Primer F | 1 nM | 2 µL |
| | | HSV-1 RVS Primer F | 3 nM | 2 µL |
| | Probe | HSV-1 Probe 1 | 1 nM | 2 µL |
| 3 | | UltraPure Water | — | 34 µL |
| | | Taq 5x Master Mix | — | 42 µL |
| | Template | HSV-2 Template | 17 nM | 2 µL |
| | | HSV-1 Template | 17 nM | 2 µL |
| | Primers | HSV-2 FWD Primer A | 100 nM | 2 µL |
| | | HSV-2 RVS Primer A | 1 nM | 2 µL |
| | | HSV-2 FWD Primer B | 40 nM | 2 µL |
| | | HSV-2 RVS Primer B | 1 nM | 2 µL |
| | | HSV-2 FWD Primer C | 3 nM | 2 µL |
| | | HSV-2 RVS Primer C | 1 nM | 2 µL |
| | | HSV-1 FWD Primer D | 1 nM | 2 µL |
| | | HSV-1 RVS Primer D | 100 nM | 2 µL |
| | | HSV-1 FWD Primer E | 1 nM | 2 µL |
| | | HSV-1 RVS Primer E | 40 nM | 2 µL |
| | | HSV-1 FWD Primer F | 1 nM | 2 µL |
| | | HSV-1 RVS Primer F | 3 nM | 2 µL |
| | Probe | HSV-2 Probe 1 | 1 nM | 2 µL |
| | | HSV-1 Probe 1 | 1 nM | 2 µL |

The signal generated from PCR reactions 1-3 is measured in arbitrary fluorescence units (AFU) and plotted as a function of number of cycles. A typical curve generated by a uniplex PCR reaction (for example reaction 1 and 2) is shown in FIG. 5.

A typical curve generated from a multiplex PCR reaction of the disclosure (for example, from reaction 3 where two targets are present in a single multiplexed reaction) is shown in FIG. 6. The curves generated are analyzed by curve fitting algorithms. These algorithms calculate the slope of the reaction in its linear regime. Each target present in these multiplexed reactions can be uniquely identified as long as the curves are in the linear dynamic range of the fluorometer.

Example 3

Generation of Characteristic Curves

FIG. 5 shows three consecutive plateaus separated by normal amplification regions. Such plot may be generated by the different reactions depending on the starting reagents.
(i) Three independent sequences, A, B, and C are present at the same time and addressed by standard PCR with a single intercalator dye and symmetric primers optimized for maximal exponential performance but designed in such a way that they hybridize at different temperatures. The reaction is programmed in such a way that it runs for the first third of the cycles at hybridization temperature for the primers of sequence A, which is too high for the primers of B and C to hybridize. The second third of the cycles is then run at the temperature suitable for the primers of B to hybridize but still too hot for the primers of C. Finally, the final third of the cycles are run at temperature low enough for C to hybridize. As there is normal amplification in the first third of the cycles, the conclusion is that A is present. As there is normal amplification in the second third of the cycles, the conclusion is that B is present. As there is normal amplification in the final third of the cycles, the conclusion is that C is present. Thus this curve decodes to positive results for A, B, and C under this setup. If any of the plateaus were missing, we would conclude that the respective sequences were missing.

(ii) A multiplex PCR reactions contains a nested set of two pairs of symmetric primers A and B for sequence #1 and a normal set of primer C for sequence #2. The outer primers of sequence #1 A have the highest melting temperature, followed by the inner primers sequence #1 B, followed by the primer C of sequence #2. The PCR program runs the first third at hybridization temperature that allows only the outer set of primers to sequence #1 to hybridize, leading to normal symmetric exponential amplification for the outer set of sequence #1. The reaction saturates by the end of the first third of the cycles. Then the program lowers the hybridization temperature so that the inner pair hybridizes but it is still too hot for the primers of sequence #2. Thus the second third sees normal symmetric exponential amplification of the inner primers. Finally, in the end third of the cycles, the temperature is low enough for sequence #2 to amplify symmetrically and exponentially and saturate by the end of the reaction. Looking at the curve and the reagent setup, it is concluded that both sequences are present.

(iii) Three pairs of nested primers A, B, and C are used for the same sequence. A, B, and C in the graph indicate the correct workings of the assay and the successful detection of the sequence. The use of three pairs of nested primers as opposed to just one primer pair may provide increased reliability. For example, if a single pair of primer is used, and the primers misprime on another sequence, e.g. in genomic DNA, amplification would still happen and the intercalator dye would report it, resulting in a false positive. This may not be possible when nested primer pairs are used because not all plateaus will be present. For example, if the sequence is not present but the outermost pair misprimes, A will be seen as normal, but B and C will not happen, so the results would be negative.

FIG. 6 can be interpreted in very similar terms as described above for FIG. 5, except that the amplification is linear asymmetric, so the respective coding is by asymmetrically chosen primer pairs. The difference between A and D is the concentration of the limiting primer, which can be used as a coding method. For example, if the curve looks like DEF instead of ABC, then a different set of target sequences has been detected using the same multiplexed assay.

Example 4

Discrimination of Curves by Basis Transformation

Figure 7:
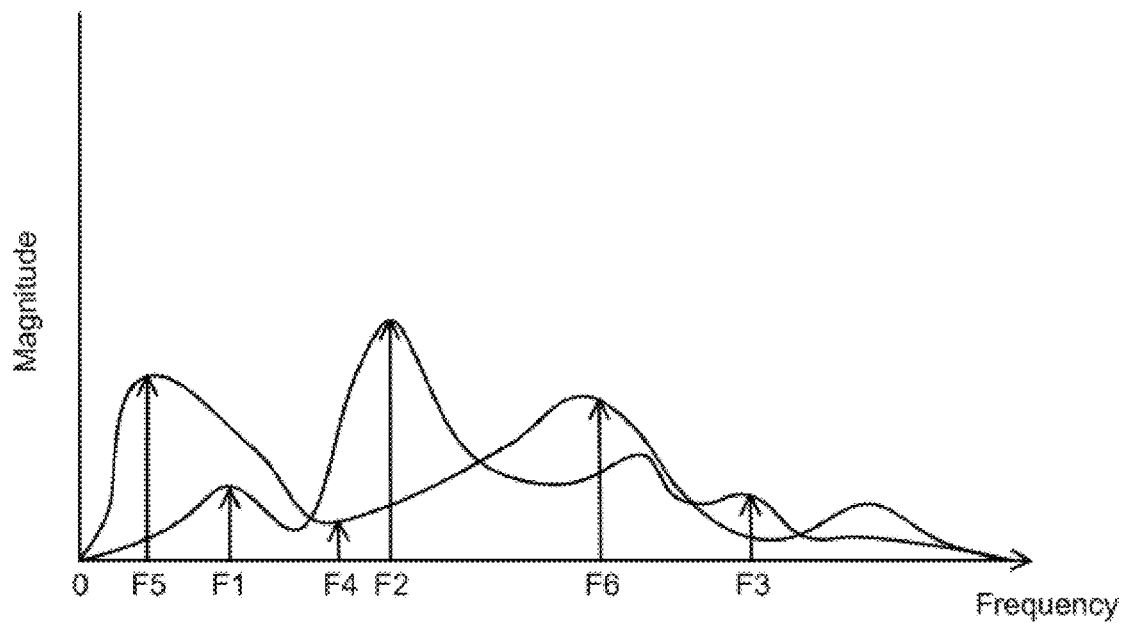
FIG. 7 shows the characteristic fluorescence curves (curve ABC and curve DEF) of two polymerase chain reactions transformed into the frequency domain.

The qPCR signals generated from a 3-target multiplexed qPCR assay similar to the one in Example 2 are transformed using a basis transformation to obtain frequency space signatures for the reactions. These frequency space signatures may be used to resolve which targets are present. In this example, Target 1 has a unique signature that is reproducible across qPCR reaction replicates. The target is identified by a specific (height, width) tuple that is specific only to Target 1. For this multiplexed reaction chemistry, a single peak signature of (0.096, 14) identifies Target 1. Furthermore, Target 2 has a distinct signature from Target 1. When Target 2 is present with this qPCR reaction chemistry, the kinetic signature observed is a dual peak curve with (height, width) tuples of (0.01, 7) and (0.1, 10). Furthermore, when Targets 1 and 2 are present in a qPCR reaction with this multiplex assay, the generated kinetic signature is unique and highly reproducible. In this example, the signature is dual peaked with (height, width) tuples of (0.018, 7) and (0.09, 12). With this example assay set, we demonstrate the proof-of-principle of unambiguous discrimination of targets using basis-transformed qPCR signals. Another typical frequency space signature obtained from the multiplexed PCR reactions of the disclosure is shown in FIG. 7.

Example 5

Detection of One or More Nucleic Acid Analytes

This example illustrates a method for the detection of one or more of a nucleic acid analyte in a sample.

In one aspect, the presence or absence of a target nucleic acid analyte in a sample is detected. An amplification reaction is performed on the sample and a signal generated during the amplification reaction is measured. A kinetic signature is generated from the measured signal, which is compared to a reference signature to determine whether the generated kinetic signature corresponds to the reference signature. Comparison of the generated kinetic signature to the reference signature allows for detection of the presence or absence of the target nucleic acid analyte in the sample. For example, a nucleic acid analyte is determined to be present in a sample if the generated kinetic signature corresponds to the reference signature. Conversely, a nucleic acid analyte is determined to be absent if the generated kinetic signature does not correspond to the reference signature.

In another aspect, the presence or absence of each of a plurality of target nucleic acid analytes in a sample is detected. A primer set is added to the sample that comprises at least two primer pairs. At least one of the primer pairs comprises a limiting primer, and each primer pair defines a region of one of the target nucleic acid analytes to be amplified. An amplification reaction is performed on the sample and a signal generated during the amplification reaction is measured. The measured signal is used to determine the presence or absence of the each of the plurality of target nucleic acid analytes. In some aspects, the concentration of a limiting primer may be sufficiently lower relative to other primers in the amplification reaction so as to affect the generated signal. For example, where the generated signal is plotted as an amplification curve, the concentration of the limiting primer may be sufficiently lower such that the generated amplification curve is not sigmoidal.

In yet another aspect, the presence or absence of two or more of a plurality of target nucleic acids in a sample is detected. A first and second primer pair is added to the sample, each primer pair defining a region of a nucleic acid analyte and having a first annealing temperature and a second annealing temperature, respectively. A thermocycling amplification reaction is performed on the sample. The thermocycling amplification reaction comprises a set of temperature cycles. At least one temperature cycle is performed that has a minimum temperature, i.e. an annealing temperature, that is not greater than the annealing temperature of the first primer pair that corresponds to the first annealing temperature, but is greater than the annealing temperature of the second primer pair, i.e. the second annealing temperature. At least one other temperature cycle is performed that has a minimum temperature, i.e. an annealing temperature, that is not greater than the annealing temperature of the second primer pair, i.e. the second annealing temperature. A signal generated during the amplification reaction is measured, and the measured signal is used to determine the presence or absence of each of the two or more of a plurality of target nucleic acid analytes.

Unless the context requires otherwise, throughout the present specification and claims, the word "comprise" and variations thereof, such as, "comprises" and "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting the presence or absence of a target nucleic acid analyte in a sample, the method comprising:
    a) performing a polymerase chain reaction (PCR) amplification reaction on the sample;
    b) measuring a signal generated during the amplification reaction and generating a kinetic signature from the measured signal; and
    c) comparing the generated kinetic signature to a reference signature and determining whether the generated kinetic signature corresponds with the reference signature, thereby detecting the presence or absence of the target nucleic acid analyte in the sample,
        wherein the reference signature corresponds with a kinetic signature generated by amplification of the target nucleic acid analyte under a set of constrained amplification parameters, the set of constrained parameters comprising one or more of (A) a range of forward and/or reverse primer concentrations; (B) chromophore concentration; and (C) chromophore type and wherein the amplification reaction is carried out within one or more of the constrained amplification parameters.

2. The method of claim 1, wherein the kinetic signature comprises a signal selected from an electromagnetic signal, a wavelength, and a fluorescence emission signal.

3. The method of claim 1, wherein the set of constrained parameters further comprises any combination of: (i) a range of polymerase concentrations; (ii) polymerase type; (iii) a range of nucleotide concentrations; (iv) a number of thermocycles; (v) rate of thermocycling; (vi) one or more thermocycle stage temperatures; (vii) one or more thermocycle stage time lengths; (viii) a range of target-specific molecular probes; (ix) primers associated with one or more target-specific probes; and (x) a concentration of one or more enzyme cofactors.

* * * * *